(12) United States Patent
Petasis

(10) Patent No.: US 7,582,785 B2
(45) Date of Patent: *Sep. 1, 2009

(54) TRIHYDROXY POLYUNSATURATED EICOSANOID DERIVATIVES

(75) Inventor: Nicos A. Petasis, Hacienda Heights, CA (US)

(73) Assignee: University of Southern California, Los Angeles, CA (US)

( * ) Notice: Subject to any disclaimer, the term of this patent is extended or adjusted under 35 U.S.C. 154(b) by 433 days.

This patent is subject to a terminal disclaimer.

(21) Appl. No.: 11/093,757

(22) Filed: Mar. 29, 2005

(65) Prior Publication Data

US 2005/0228047 A1 Oct. 13, 2005

Related U.S. Application Data

(63) Continuation-in-part of application No. 10/405,924, filed on Apr. 1, 2003, now Pat. No. 6,949,664.

(60) Provisional application No. 60/369,543, filed on Apr. 1, 2002.

(51) Int. Cl.
 *C07C 57/00* (2006.01)
(52) U.S. Cl. ..................................... 554/224
(58) Field of Classification Search ............... None
 See application file for complete search history.

(56) References Cited

U.S. PATENT DOCUMENTS

| | | | |
|---|---|---|---|
| 4,442,099 A | 4/1984 | Nicolaou et al. |
| 4,567,290 A | 1/1986 | Nicolaou et al. |
| 4,576,758 A | 3/1986 | Morris et al. |
| 4,710,521 A | 12/1987 | Soukup et al. |
| 4,759,880 A | 7/1988 | Nicolaou et al. |
| 5,087,790 A | 2/1992 | Petasis et al. |
| 5,136,501 A | 8/1992 | Silverman et al. |
| 5,177,046 A | 1/1993 | Savoca et al. |
| 5,409,955 A | 4/1995 | Bockow et al. |
| 5,594,732 A | 1/1997 | Bell et al. |
| 5,650,157 A | 7/1997 | Bockow |
| 5,752,238 A | 5/1998 | Dedrick |
| 5,756,789 A | 5/1998 | Bruce et al. |
| 5,842,040 A | 11/1998 | Hughes et al. |
| 5,845,265 A | 12/1998 | Woolston |
| 5,861,399 A | 1/1999 | Seed et al. |
| 5,870,717 A | 2/1999 | Wiecha |
| 5,878,400 A | 3/1999 | Carter, III |
| 5,878,423 A | 3/1999 | Anderson et al. |
| 5,890,138 A | 3/1999 | Godin et al. |
| 5,896,379 A | 4/1999 | Haber |
| 5,912,006 A | 6/1999 | Bockow et al. |
| 5,946,467 A | 8/1999 | Pathakis et al. |
| 6,030,715 A | 2/2000 | Thompson et al. |
| 6,030,917 A | 2/2000 | Weinberg et al. |
| 6,069,109 A | 5/2000 | Kao et al. |
| 6,232,467 B1 | 5/2001 | Petasis et al. |
| 6,259,699 B1 | 7/2001 | Opalka et al. |
| 6,272,474 B1 | 8/2001 | Garcia |
| 6,336,105 B1 | 1/2002 | Conklin et al. |
| 6,336,138 B1 | 1/2002 | Caswell et al. |
| 6,377,937 B1 | 4/2002 | Paskowitz |
| 6,397,212 B1 | 5/2002 | Biffar |
| 6,415,270 B1 | 7/2002 | Rackson et al. |
| 6,427,132 B1 | 7/2002 | Bowman-Amuah |
| 6,602,817 B1 | 8/2003 | Petasis |
| 6,670,396 B2 | 12/2003 | Serhan et al. |
| 6,949,664 B2 * | 9/2005 | Petasis ........................ 554/224 |
| 7,030,159 B2 | 4/2006 | Serhan et al. |
| 7,053,230 B2 | 5/2006 | Serhan et al. |
| 7,341,840 B2 | 3/2008 | Serhan et al. |
| 2002/0055539 A1 | 5/2002 | Bockow et al. |
| 2002/0111505 A1 | 8/2002 | Serhan |
| 2003/0236423 A1 | 12/2003 | Petasis |
| 2004/0044050 A1 | 3/2004 | Goodman et al. |
| 2004/0116408 A1 | 6/2004 | Serhan |
| 2005/0228047 A1 | 10/2005 | Petasis |
| 2005/0261255 A1 | 11/2005 | Serhan et al. |
| 2006/0128804 A1 | 6/2006 | Serhan et al. |

(Continued)

FOREIGN PATENT DOCUMENTS

EP 0 736 509 A2 10/1996

(Continued)

OTHER PUBLICATIONS

Alami et al., A versatile route to conjugated hydroxy (E,Z,E,E)-tetraenoic acids: highly chemo- and stereoselective synthesis of lipoxin $B_4$ *Tetrahedron Asym.* 8(17): 2949-2958, 1997.

(Continued)

*Primary Examiner*—Deborah D Carr
(74) *Attorney, Agent, or Firm*—Scott D. Rothenberger; Fulbright & Jaworski LLP

(57) ABSTRACT

The invention features methods for the preparation of naturally occurring trihydroxy polyunsaturated eicosanoids and their structural analogs. The invention further provides new derivatives and analogs of trihydroxy polyunsaturated eicosanoids that can be prepared according to these methods. The invention also provides compositions and methods using trihydroxy polyunsaturated eicosanoid derivatives for the prevention, amelioration and treatment of a variety of diseases or conditions associated with inflammation or inflammatory response, autoimmune diseases, rheumatoid arthritis, cardiovascular diseases, or abnormal cell proliferation or cancer.

18 Claims, No Drawings

U.S. PATENT DOCUMENTS

| | | | |
|---|---|---|---|
| 2006/0293288 | A1 | 12/2006 | Serhan et al. |
| 2008/0096961 | A1 | 4/2008 | Serhan et al. |

FOREIGN PATENT DOCUMENTS

| | | | |
|---|---|---|---|
| EP | 0 736 509 | B1 | 11/2001 |
| GB | 2033745 | A | 5/1980 |
| WO | 9846588 | A1 | 10/1988 |
| WO | 9116914 | A1 | 11/1991 |
| WO | WO 97/19415 | | 5/1997 |
| WO | WO 98/19259 | | 5/1998 |
| WO | WO 98/35469 | | 8/1998 |
| WO | WO 99/06913 | | 2/1999 |
| WO | WO 99/13417 | | 3/1999 |
| WO | WO 00/74632 | | 6/1999 |
| WO | 9956727 | A2 | 11/1999 |
| WO | 9956727 | A3 | 11/1999 |
| WO | 0032210 | A1 | 6/2000 |
| WO | WO 01/60778 | | 8/2001 |
| WO | WO 03/084305 | A | 10/2003 |
| WO | WO 03/105776 | | 12/2003 |
| WO | WO 03/105776 | A | 12/2003 |
| WO | WO 2005/089744 | A | 9/2005 |

OTHER PUBLICATIONS

Babine, R. E. and S.L. Bender., "Molecular Recognition of Protein-Ligand Complexes: Applications to Drug Design," *Chem. Rev.* 97:1359-1472 (1997).

Bhaley, G. et al., "Solid-Phase Synthesis of Diverse Tetrahydro-1,4-Benzodiazepine-2-ones," *Tetrahedron Letters* 38(48):8375-8378 (1997).

Bläser, E. et al., "Asymmetric Steering of OXA Diels—Alder Reactions with Silyloxydienes Employing Proline Esters as Chiral Auxiliary Groups," *Eur. J. Org. Chem.*, 329-333, (1999).

Boland et al., "Stereospecific Syntheses and Spectroscopic Properties of Isomeric 2,4,6,8-Undecatetraenes. New Hydrocarbons from the Marine Brown Alga *Giffordia mitchellae*", *Helv. Chim. Acta* 70: 1025-1040, 1987.

Deloux, Laurent and Morris Srebnik "Asymmetric Boron-Catalyzed Reactions", *Chem. Rev.* 93:763-784, (1993).

Durantel et al., "Study of the Mechanism of Antiviral Action of Iminosugar Derivatives against Bovine Viral Diarrhea Virus," *J. Virology* 75(19): 8987-8998, (2001).

Du Bois et al., "Novel, Stereoselective Synthesis of 2-Amino Saccharides," *J. Am. Chem. Soc.* 119:3179-3180, 1997.

Evans, B.E. et al., "Design of Nonpeptidal Ligands for a Peptide Receptor: Cholecystokinin Antagonists," *J. Med. Chem.* 30:1229-1239 (1987).

Fletcher, M. D. and M.C. Campbell, "Partially Modified Retro-Inverso Peptides: Development, Synthesis, and Conformational Behavior," *Chem. Rev.*, 98:763-795, (1998).

Garro-Helion et al., "Mild and Selective Palladium(0)-Catalyzed Deallylation of Allylic Amines. Allylamine and Diallylamine as Very Convenient Ammonia Equivalents for the Synthesis of Primary Amines," *J. Org. Chem.*, 58:6109-6113, (1993).

Golebiowski, A. and J. Jurczak, "α-Amino-β-hydroxy Acids in the Total Synthesis of Amino Sugars," *Synlett*, pp. 241-245, (Apr. 1993).

Guillier et al., "Linkers and Cleavage Strategies in Solid-Phase Organic Synthesis and Combinatorial Chemistry," *Chem. Rev.*, 100:2091-2157, (2000).

Hanessian, S. et al., "Design and Synthesis of Conformationally Constrained Amino Acids as Versatile Scaffolds and Peptide Manners," *Tetrahedron*, 53:12789-12854, (1997).

Hoyng, C.F. and A.D. Patel, "Aldehyde Components for Use in Four-Component Condensation ("4CC") UGI Reaction Peptide Synthesis," *Tetrahedron Lett.*, 21:4795-4798, (1980).

Humphrey, J.M. and A.R. Chamberlin, "Chemical Synthesis of Natural Product Peptides: Coupling Methods for the Incorporation of Noncoded Amino Acids into Peptides," *Chem. Rev.*, 97:2243-2266, (1997).

Ikeda et al, "Chiral Allenylboronic Esters as a Practical Reagent for Enantioselective Carbon-Carbon Bond formation Facile Synthesis of (-)Ipsenol" *J. Am. Chem. Soc.* 108: 483-486, 1986.

König et al., "Synthesis of N-tert-Alkylglyoxylic Acid Amides," *Synthesis*, pp. 1233-1234, (1993) [in German, English language abstract on 1$^{st}$ page of article].

Marx et al., "Synthetic Design for Combinatorial Chemistry. Solution and Polymer-Supported Synthesis of Polycyclic Lactams by Intramolecular Cyclization of Azomethine Ylides," *J. Am. Chem. Soc.*, 119:6153-6167, (1997).

Mehta et al., "Structure-Activity Relationship of a New Class of Anti-Hepatitis B Virus Agents," *Antimicrobial Agents and Chemotherapy*, 46(12):4004-4008 (2002).

Nicolaou et al., "Novel IBX-Mediated Process for the Synthesis of Amino Sugars and Libraries Thereof," *Angew. Chem. Int. Ed. Engl.*, 39:2525-2529, (2000).

Nicolaou et al., "Lipoxins and Related Eicosanoids: Biosynthesis, Biological Properties, and Chemical Synthesis," *Angew. Chem. Int. Ed. Engl.* 30:1100-1116, (1991).

Noyori, R. (Ed.), "Enantioselective Addition of Organometallic Reagents to Carbonyl Compounds: Chirality Transfer, Multiplication, and Amplification," Chapter 5 in *Asymmetrical Catalysis in Organic Synthesis*, New York: John Wiley & Sons, Inc., pp. 255-297 (1994).

Nugent, William A., "Chiral Lewis Acid Catalysis. Enantioselective Addition of Azide to Meso Epoxides", *J. Am. Chem. Soc.*, 114(7): 2768-2769 (1992).

O'Donnell, Martin J. and J. Falmagne, "The Synthesis of Amino Acids via Organoboranes." *J. Chem. Soc. Chem. Commun.*, No. 17, pp. 1168-1169, (Sep. 1, 1985).

J.W. Karanian et al., "Inhibitory Effects of n-6 and n-3 Hydroxy Fatty Acids on Thromboxane (U46619)-Induced Smooth Muscle Contraction", J. of Pharmacology and Experimental Therapeutics,vol. 270. No. 3, pp. 1105-1109 (1994).

Khalfoun, B. et al., "Docosahexaenoic and Eicosapentaenoic Acids Inhibit Human Lymphoproliferative Responses In Vitro but not the Expression of T cells Surface Activation Markers", Scand. J. Immunology, 43, pp. 248-256, 1996, XP-0000878923.

Croset, M. et al., "Inhibition by Lipoxygenase Products of TXA2-Like Responses of Platelets and Vascular Smooth Muscle", Biochemical Pharmacology, vol. 37, No. 7, pp. 1275-1280, 1988, XP-002445509.

"Epolinsatures", Bulletin De La Societe Chimique de France, No. 3, pp. 419-432, 1989.

Hill, E.M., *Proc R. Soc. London Ser. B.*, 247 (1318) 1992, pp. 41-46.

Khair-El-Din et al., "Transcription of the murine INOS gene is inhibited by docosahexanaenoic acid, a major constituent of fetal serum and fish oils diets inhibits IFN alpha-induced la-expression by murine macrophases in vitro", *J. Immuno.*, vol. 154, 1995, pp. 1296-1306.

Levy, Bruce D. et al. "Protectin D1 is Generated in Asthma and Dampens Airway Inflammation and Hyperresponsiveness," *The Journal of Immunology*, 2007, 178: 496-502.

Miller et al., "Guinea Pig Epidermis Generates Putative Anti-Inflammatory Metabolites from Fish Oil Polyunsaturated Fatty Acids", Lipids, Chemical Abstract 24(12), 112: 117062, pp. 998-1003, 1989. Lipids, Chemical Abstract 112:117062, 1989, pp. 998-1003.

Serhan et al., "Novel functional sets of lipid-derived mediators with Anti-inflammatory Actions generated from omega-3 fatty acids via cyclooxygenase 2-nonsteroidal anti-inflammatory drugs and transcellular processing", *J. Exp. Med.*, vol. 192, No. 8, 2000, pp. 1197-1204.

Serhan, et al. "Resolvins, Docosatrienes, and Neuroprotectins, Novel Omega-3-Derived Mediators, and their Endogenous Aspirin-Triggered Epimers", *Lipids*, 73: 155-172, 2004.

Chemical Abstracts online citation, AN:2004:143088, retrieved Aug. 15, 2007, from STN, Columbus, OH.

Hong, et al. "Rainbow trout (*Oncorhynchus mykiss*) brain cells biosynthesize novel docasahexaenoic acid-derived resolvins and protectins—mediator lipidomic analysis", *Prostaglandins & Other Lipid Mediators*, Elsevier, vol. 78, No. 1-4, Jun. 13, 2005, pp. 107-116. XP005174168.

Serhan, Charles N. et al. "Anti-Inflammatory Actions of Neuroprotectin D1/Protectin D1 and it's Natural Stereoisomers:

Assignments of Dihydroxy-Containing Docosatrienes", Journal of Immunology, 176(3), 1848-1959 Coden: J0IMA3; ISSN 0022-1767, Feb. 1, 2006. XP002429095.

PCT/US2006/038326 International Search Report dated Apr. 23, 2007.

PCT/US2006/000306 International Search Report dated Jul. 14, 2006.

PCT/US2003/25336 International Search Report dated Feb. 16, 2004.

PCT/US2001/05196 International Search Report dated Jul. 19, 2002.

EP 06 02 2386 European Search Report dated Oct. 5, 2007.

PCT/US2005/12552 International Search Report dated Aug. 24, 2005 (in name of Trustees of Boston University).

PCT/US2006/011222 International Search Report dated Oct. 5, 2007.

PCT/US2005/009056 International Search Report dated Nov. 16, 2005.

Slots, et al., "General Health Risk of Periodontal Disease", International Dental Journal, Dec. 2001, 51(6), pp. 417-422.

Green, Gary A., "Understanding NSAIDS: From Aspirin to COX-2", Clinical Cornerstone, Sports Medicine 2001, 3(5), pp. 50-59.

Merck Index, "Gingivitis", Copyright © 1995-2007 Merck & Co., Inc., Whitehouse Station, NJ, USA, Last Full Version, Feb. 2003, 3 pgs.

Stella, Valentino J., "Expert Opinion of Therapeutic Patents", Prodrugs as Therapeutics, 2004, 14(3), pp. 277-280.

Wolff et al., "Burger's Medicinal Chemistry and Drug Discovery", $5^{th}$ Ed., vol. 1, pp. 975-977, 1994.

Dragoli et al., "Parallel Synthesis of Prostaglandin $E_1$ Analogues", J. Comb. Chem., 1999, pp. 534-539.

Petasis, N. A. and I.A. Zavialov, "The Boronic Acid Mannich Reaction: A New Method for the Synthesis of Geometrically Pure Allylamines." Tetrahedron Letters, 34(4):583-586, (1993).

Petasis, N.A. and I.A. Zavialov, "A New and Practical Synthesis of α-Amino Acids from Alkenyl Boronic Acids," *J. Am. Chem. Soc.*, 119(2):445-446, (1997).

Rodriguez and Spur, "Total synthesis of aspirin-triggered 15-*epi*-lipoxin $A_4$" *Tetrahedron Lett.*, 42: 6057-6060, 2001.

"Scope and Editorial Policy," *Organometallics*, published by the American Chemical Society 21(1):13A, 14A (2002).

Serhan et al., "Novel Functional Sets of Lipid-derived Mediators with Antiinflammatory Actions Generated from Omega-3 Fatty Acids via Cyclooxygenase 2-Nonsteroidal Antiinfammatory Drugs and Transcellular Processing," *J. Exp. Med.* 192:1197-1204, (2000).

Serhan et al., "Resolvins: A Family of Bioactive Products of Omega-3 Fatty Acid Transformation Circuits Initiated by Aspirin Treatment that Counter Proinflammation Signals" *J. Exp. Med.* 196: 1025-1037, 2002.

Serhan, "A search for endogenous mechanisms of anti-inflammation uncovers novel chemical mediators: missing links to resolution", *Histochem. Cell Biol*, 122: 305-321, 2004.

Thompson, L.A. and J.A. Ellman, "Synthesis and Applications of Small Molecule Libraries," *Chem. Rev.* 96:555-600 (1996).

Waki, M. and J. Meienhofer, "Peptide Synthesis Using the Four-Component Condensation (Ugi Reaction)," *J. Am. Chem. Soc.*, 99:6075-6082, (1977).

Yamamoto, Y. and N. Asao, "Selective Reactions Using Allylic Metals." *Chem. Rev.*, 93:2207-2293, (1993).

\* cited by examiner

TRIHYDROXY POLYUNSATURATED EICOSANOID DERIVATIVES

RELATED APPLICATIONS

This application is a continuation-in-part of allowed U.S. application Ser. No. 10/405,924, filed on Apr. 1, 2003 now U.S. Pat. No. 6,949,664. U.S. application Ser. No. 10/405,924 claims benefit of priority under 35 U.S.C. §119(e) to and U.S. Provisional Patent Application Ser. No. 60/369,543, filed on Apr. 1, 2002. The content of each of these applications is hereby incorporated in its entirety by reference.

STATEMENT REGARDING FEDERALLY SPONSORED RESEARCH

The U.S. Government may have certain rights in this invention pursuant to Grant No. PO1-DE13499 (Subcontract) awarded by the National Institutes of Health.

FIELD OF THE INVENTION

This invention relates to trihydroxy polyunsaturated eicosanoid derivatives and methods for the preparation of such compounds and their structural analogs. This invention also relates to compounds, compositions and methods using trihydroxy polyunsaturated eicosanoid derivatives for the prevention, amelioration and treatment of a variety of diseases or conditions associated with inflammation or inflammatory response, autoimmune diseases, rheumatoid arthritis, cardiovascular diseases, or abnormal cell proliferation or cancer.

BACKGROUND OF THE INVENTION

The present invention provides methods for preparing lipid mediators related to ω-3 polyunsaturated fatty acids (PUFA), which have potential use in the development of new pharmaceuticals based on the well-established beneficial effects of PUFA.

It has long been suggested that dietary ω-3 polyunsaturated fatty acids (PUFA) (De Caterina, R., Endres, S.; Kristensen, S. D.; Schmidt, E. B., (eds). ω-3 *Fatty Acids and Vascular Disease*, Springer-Verlag, London. 166 pp. 1993; Gill, I., and Valivety, R. (1997), *Trends in Biotechnology* 15, 401-409;) have beneficial effects in human health and in the prevention of various diseases, including inflammation and autoimmune diseases (Simopoulos, A. P. (2002), *J. Am. Coll. Nutrition* 21, 495-505), rheumatoid arthritis (Cleland, L. G., James, M. J., and Proudman, S. M. (2003), *Drugs* 63, 845-853), cardiovascular diseases (Billman, G. E., et al. *Circulation*. 1999, 99, 2452; Harper, C. R., and Jacobson, T. A. (2001) *Arch. Intern. Med.* 161, 2185-2192), and cancer (Iigo, M. et al., *Br. J. Cancer*, 1997, 75, 650; Larsson, S. C., Kumlin, M., Ingelman-Sundberg, M., and Wolk, A. (2004), *Am. J. Clin. Nutr.* 79, 935-945).

Eicosapentaenoic acid (C20:5), the major PUFA in fish oil, was shown to form prostaglandins (PG), leukotrienes (LT) and other eicosanoids that are similar to those derived from arachidonic acid (C20:4). The different biological properties of these molecules were considered to be responsible for the role of PUFA. Despite numerous studies in this area, however, the molecular mechanisms for the actions of PUFA remain unknown.

The conversion of arachidonic acid (C20:4) to a variety of bioactive eicosanoids, including prostaglandins (PG), leukotrienes (LT) and lipoxins (LX) is well known (Nicolaou, K. C.; Ramphal, J. Y.; Petasis, N. A.; Serhan, C. N. *Angew. Chem. Int. Ed. Engl.* 1991, 30, 1100).

It was recently demonstrated (Serhan, C. N. et al. *J. Exp. Med.* 2000. 192, 1197) that human endothelial cells with up-regulated COX-2 treated with aspirin convert ω-3 polyunsaturated fatty acids to 18R-HEPE as well as 15R-HEPE. While 15R-HEPE led to the 5-series lipoxins (15R-LXA$_5$), 18R-HEPE led to 5S,12R,18R-triHEPE (1), a novel trihydroxy-eicosanoid related to the structure of LTB$_4$. Due to their role in the resolution of inflammation, compounds of this type were named Resolvins (Serhan, C. N.; et al., *J. Exp. Med.* 2002, 196, 1025; Serhan, C. N. (2004) Histochem Cell Biol (2004) 122:305-321), while compound 1 was named Resolvin E1.

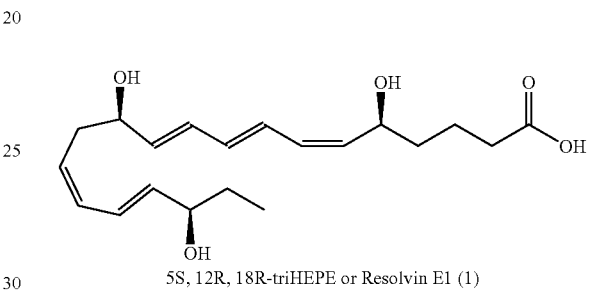

5S, 12R, 18R-triHEPE or Resolvin E1 (1)

The formation of these trihydroxy polyunsaturated eicosanoids from PUFA suggests a novel mechanism for the therapeutic benefits of PUFA with major implications for new therapeutic approaches to a variety of diseases. Methods for the preparation of such compounds, therefore, are of great importance to the development of new therapeutic agents. Furthermore, the development of structural derivatives of these compounds may be useful for the optimization of their pharmacological profile and other desirable drug-like properties.

SUMMARY

The invention features methods for the preparation of naturally occurring trihydroxy polyunsaturated eicosanoids and their structural analogs. The invention further provides new derivatives of trihydroxy polyunsaturated eicosanoids that can be prepared according to these methods.

In general, in one aspect, the invention features methods of preparing trihydroxy polyunsaturated eicosanoids, such as 1, as outlined in Scheme 1. The two (Z) C═C bonds can be formed via selective hydrogenation of the bis-alkynyl precursor 2. Compound 2 can be prepared via a palladium-mediated coupling (coupling step a) between intermediates 3 and 4, where X is Br, or I. Compound 4 can be prepared via the olefination of aldehyde 5, which is readily available from protected epoxide 6. Intermediate 3 can be prepared in several different ways, as discussed below, from precursors 7 and 8, while compound 8 can readily prepared from protected epoxide 9.

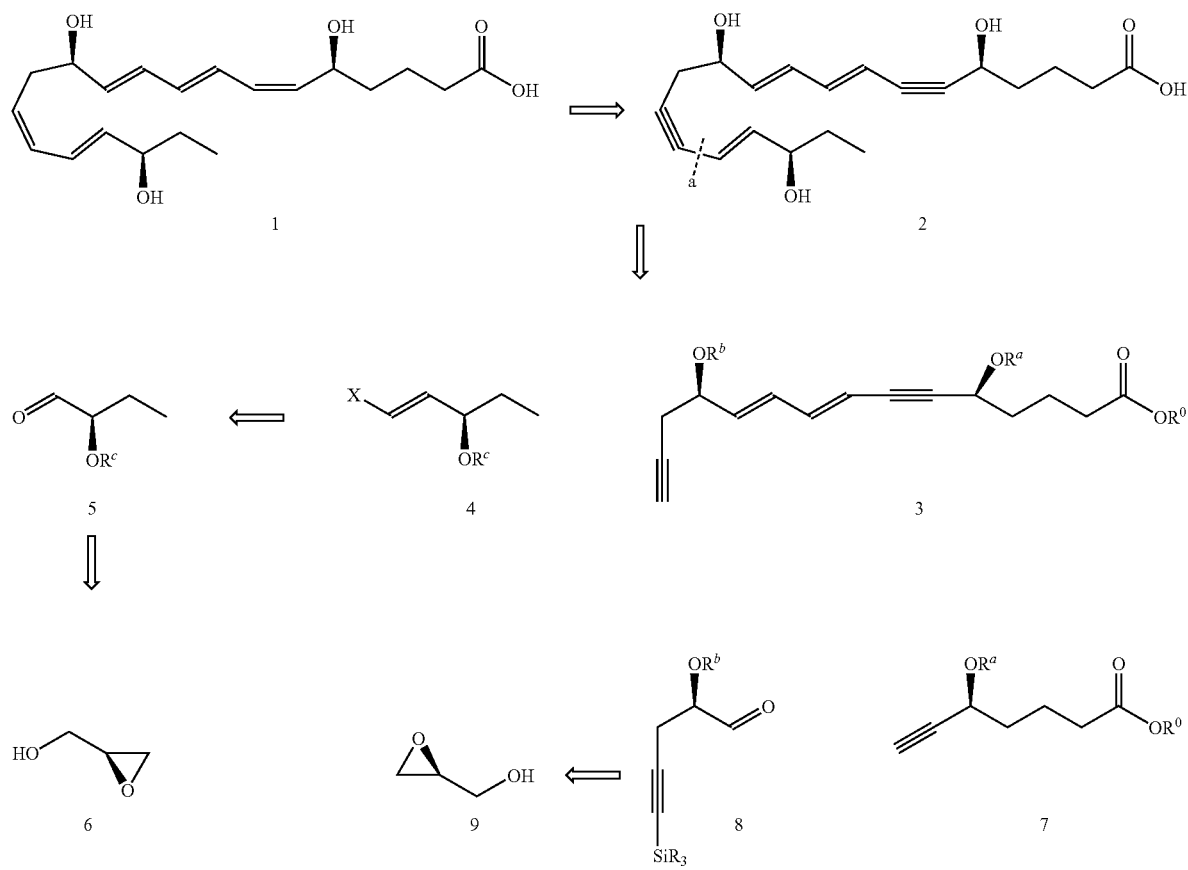
The invention also provides methods for the preparation of compounds of the general formula 3, which can be used to prepare trihydroxy polyunsaturated eicosanoids or their analogs. Compound 3 can be prepared in several different ways, as outlined in Scheme 2.
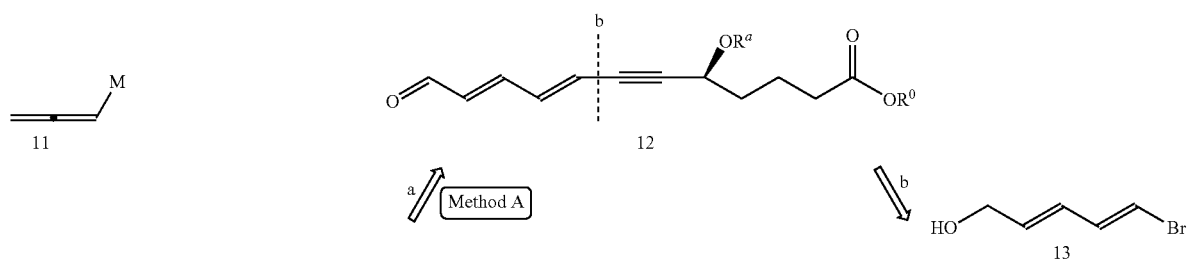

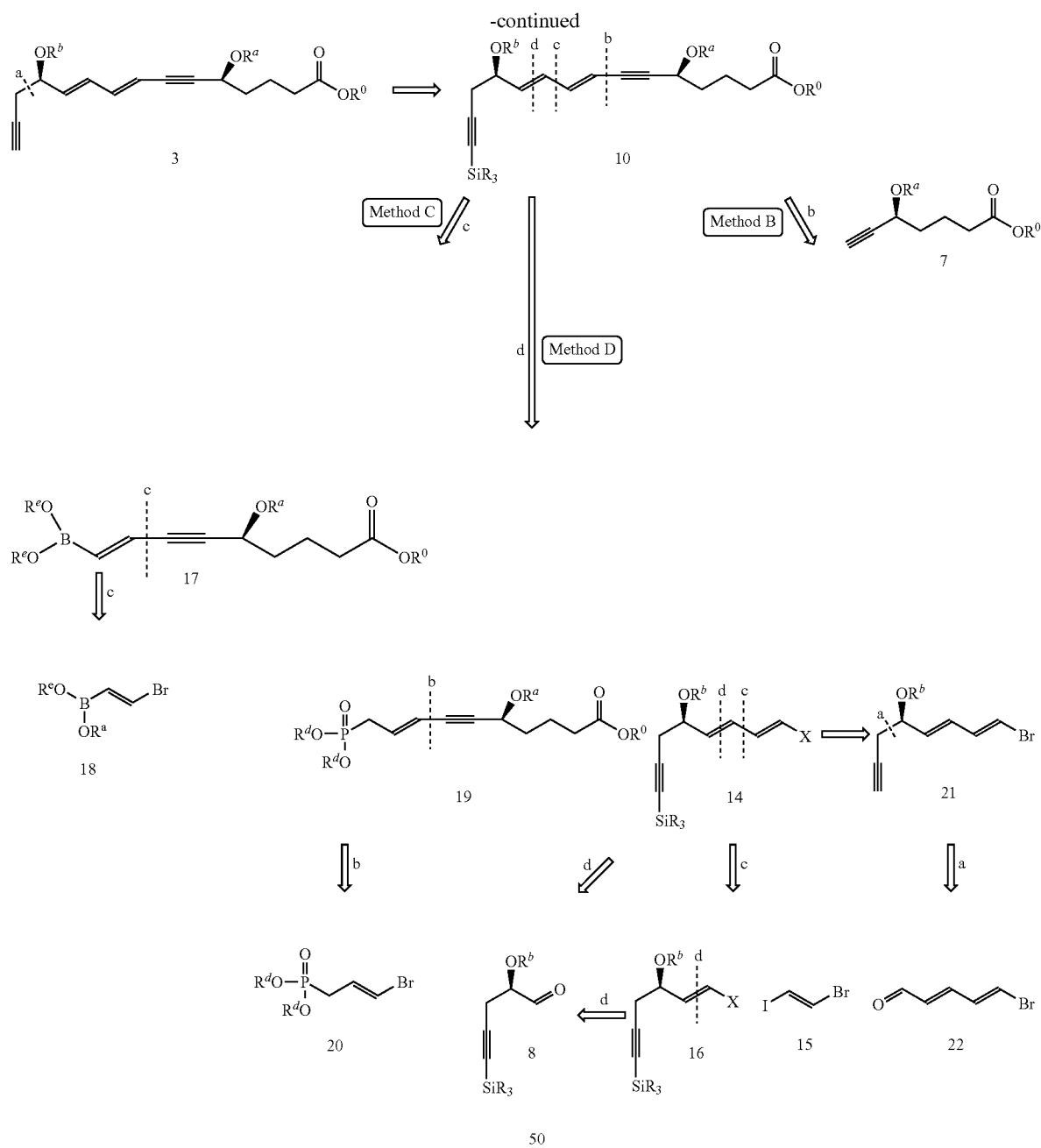

According to Method A, compound 3 can be prepared via the addition of an allenyl reagent 11 (M is magnesium, zinc, copper, tin, silicon or boron) to precursor 12, which is readily available via the Pd-coupling between the known bromide 13 and the known alkyne 7.

According to Method B, compound 3 is prepared from precursor 10, which is produced via Pd-mediated coupling (coupling process b) of 7 with intermediate 14. Compound 14, can be prepared via Pd-coupling (coupling process c) between 15 and precursor 16, which can be prepared via the olefination (coupling process d) of aldehyde intermediate 8. Alternatively, compound 14, can be prepared via a Wittig-type reaction (coupling process d) between 20 and aldehyde 8. Compound 14 can also be prepared via silylation of its alkyne precursor 21, which can be formed via addition to the aldehyde 22 (coupling process a).

According to Method C, precursor 10, is formed via the Pd-coupling (coupling process c) between 16 and alkenyl boron compound 17, which is readily available via the Pd-coupling (coupling process c) between alkenyl boron compound 18 and intermediate 7.

Finally, according to Method D, compound 10, is prepared via the alkenylation (coupling process d) of aldehyde intermediate 8 with phosphonate intermediate 19, which is readily available via the Pd-coupling (coupling process b) between the compound 20 with 7.

In another aspect, the invention features methods for the synthesis of compounds having the general formulas 23 and 24, as outlined in Scheme 3. Compound 23 can be prepared via the selective hydrogenation of compound 24, which can be produced via a Sonogasbira-type coupling among compounds 25 and 26:

Scheme 3

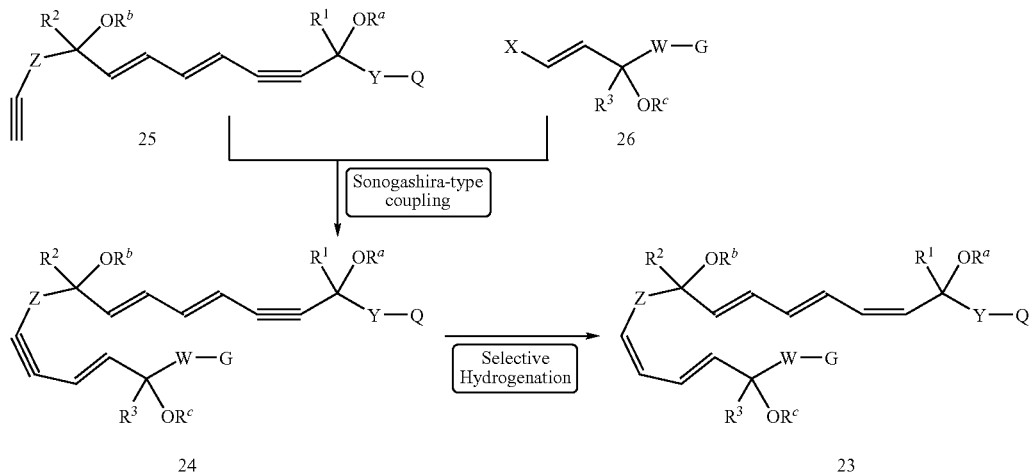

wherein:
R$^a$, R$^b$ and R$^c$, are independently selected from the group consisting of hydrogen, alkyl, aryl, heteroaryl, acyl, silyl, alkoxyacyl and aminoacyl;

R$^1$, R$^2$ and R$^3$ are independently selected from the group consisting of hydrogen, alkyl, perfluoroalkyl, aryl and heteroaryl;

Q is selected from the group consisting of:
—C(O)-A, —SO$_2$-A, —PO(OR)-A, where A is hydroxy, alkoxy, aryloxy, amino, alkylamino, dialkylamino, or —OM, where M is a cation selected from the group consisting of ammonium, tetra-alkyl ammonium, Na, K, Mg, and Zn, and R is hydroxyl or alkoxy;

Y, Z and W are linkers independently selected from the group consisting of a ring containing up to 20 atoms and a chain of up to 20 atoms, provided that Y, Z and W can independently include one or more nitrogen, oxygen, sulfur or phosphorous atoms, and further provided that Y, Z and W can independently include one or more substituents selected from the group consisting of hydrogen, alkyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, and sulfonyl, and further provided that Y, Z and W can also contain one or more fused carbocyclic, heterocyclic, aryl or heteroaryl rings, and provided that all linkers Y are connected to the adjacent C(R)OR group via a carbon atom;

X is Cl, Br or I; and

G is selected from the group consisting of hydrogen, alkyl, perfluoroalkyl, alkenyl, alkynyl, aryl, heteroaryl, chloro, iodo, bromo, fluoro, hydroxy, alkoxy, aryloxy, carboxy, amino, alkylamino, dialkylamino, acylamino, and carboxamido The invention also provides compounds and compositions containing synthetic analogs of trihydroxy polyunsaturated eicosanoids that are synthetic derivatives or analogs of compound 1 and exhibit improved chemical and biological properties. The provided compounds include derivatives having the general formulas 23 and 24:

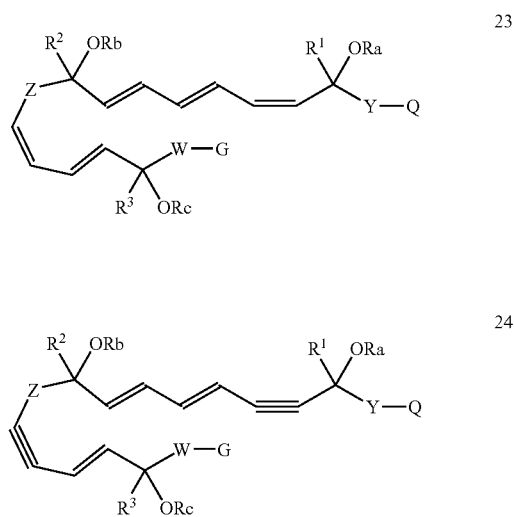

wherein,

A is hydroxy, alkoxy, aryloxy, amino, alkylamino, dialkylamino, or —OM, where M is a cation selected from a group consisting of ammonium, tetra-alkyl ammonium, Na, K, Mg, or Zn;

R$^a$, R$^b$ and R$^c$, are independently selected from a group that consists of hydrogen, alkyl, aryl, heteroaryl, acyl, silyl, alkoxyacyl or aminoacyl;

R$^1$, R$^2$ and R$^3$ are independently selected from a group that consists of hydrogen, alkyl, perfluoroalkyl, aryl or heteroaryl;

Q is selected from a group that consists of:
—C(O)-A, —SO2-A, —PO(OR)-A, where A is hydroxy, alkoxy, aryloxy, amino, alkylamino, dialkylamino, or —OM, where M is a cation selected from a group consisting of ammonium, tetra-alkyl ammonium, Na, K, Mg, or Zn; and R is hydroxyl or alkoxy;

Y, Z and W are linkers selected from a group consisting of a ring or a chain of up to 20 atoms that may include one or more nitrogen, oxygen, sulfur or phosphorous atoms, provided that linker A can have one or more substituents selected from the group consisting of hydrogen, alkyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, and sulfonyl, and further provided that the linker may also contain one or more fused rings, including carbocyclic, heterocyclic, aryl or heteroaryl rings, provided that all linkers Y are connected to the adjacent C(R)OR group via a carbon atom;

G is selected from a group that consists of hydrogen, alkyl, perfluoroalkyl, alkenyl, alkynyl, aryl, heteroaryl, chloro, iodo, bromo, fluoro, hydroxy, alkoxy, aryloxy, carboxy, amino, alkylamino, dialkylamino, acylamino, and carboxamido.

The invention also provides compounds and compositions containing synthetic analogs of trihydroxy polyunsaturated eicosanoids that are synthetic derivatives or analogs of compound 1 and exhibit improved chemical and biological properties. The provided compounds include derivatives having the general formulas 23 and 24:

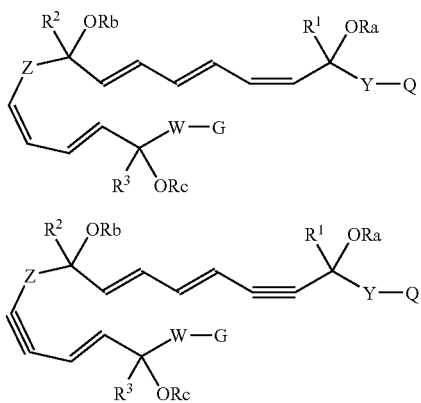

wherein,

A is hydroxy, alkoxy, aryloxy, amino, alkylamino, dialkylamino, or —OM, where M is a cation selected from a group consisting of ammonium, tetra-alkyl ammonium, Na, K, Mg, or Zn;

$R^a$, $R^b$ and $R^c$, are independently selected from a group that consists of hydrogen, alkyl, aryl, heteroaryl, acyl, silyl, alkoxyacyl or aminoacyl;

$R^1$, $R^2$ and $R^3$ are independently selected from a group that consists of hydrogen, alkyl, perfluoroalkyl, aryl or heteroaryl;

Q is selected from a group that consists of:
—C(O)-A, —SO2-A, —PO(OR)-A, where A is hydroxy, alkoxy, aryloxy, amino, alkylamino, dialkylamino, or —OM, where M is a cation selected from a group consisting of ammonium, tetra-alkyl ammonium, Na, K, Mg, or Zn; and R is hydroxyl or alkoxy;

Y, Z and W are linkers selected from a group consisting of a ring or a chain of up to 20 atoms that may include one or more nitrogen, oxygen, sulfur or phosphorous atoms, provided that linker A can have one or more substituents selected from the group consisting of hydrogen, alkyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, and sulfonyl, and further provided that the linker may also contain one or more fused rings, including carbocyclic, heterocyclic, aryl or heteroaryl rings, provided that all linkers Y are connected to the adjacent C(R)OR group via a carbon atom;

G is selected from a group that consists of hydrogen, alkyl, perfluoroalkyl, alkenyl, alkynyl, aryl, heteroaryl, chloro, iodo, bromo, fluoro, hydroxy, alkoxy, aryloxy, carboxy, amino, alkylamino, dialkylamino, acylamino, and carboxamido.

In other aspects, the invention also features pharmaceutical compositions including the compounds of the invention, as well as therapeutic uses for such compounds and compositions in treating and/or preventing a disease or condition associated with inflammation or inflammatory response, autoimmune diseases, rheumatoid arthritis, cardiovascular diseases, or abnormal cell proliferation or cancer.

The details of one or more embodiments of the invention are set forth in the description below. Unless otherwise defined, all technical and scientific terms used herein have the meaning commonly understood by one of ordinary skill in the art to which this invention belongs. All publications, patent applications, patents, and other references mentioned herein are incorporated by reference in their entirety. In case of conflict, the present specification, including definitions, will control. Other features and advantages of the invention will become apparent from the description and the claims.

DETAILED DESCRIPTION OF THE INVENTION

Definitions

As used in this specification, alkyl groups can include straight-chained, branched and cyclic alkyl radicals containing up to about 20 carbons. Suitable alkyl groups may be saturated or unsaturated. Further, an alkyl may also be substituted one or more times on one or more carbons with one or more substituents selected from the group consisting of C1-C6 alkyl, C3-C6 heterocycle, aryl, halo, hydroxy, amino, alkoxy and sulfonyl. Additionally, an alkyl group may contain up to 10 heteroatoms or heteroatom substituents. Suitable heteroatoms include nitrogen, oxygen, sulfur and phosphorous.

As used in this specification, aryl groups are aryl radicals which may contain up to 10 heteroatoms. An aryl group may also be optionally substituted one or more times with an aryl group or a lower alkyl group and it may be also fused to other aryl or cycloalkyl rings. Suitable aryl groups include, for example, phenyl, naphthyl, tolyl, imidazolyl, pyridyl, pyrroyl, thienyl, pyrimidyl, thiazolyl and furyl groups.

As used in this specification, a ring is defined as having up to 20 atoms that may include one or more nitrogen, oxygen, sulfur or phosphorous atoms, provided that the ring can have one or more substituents selected from the group consisting of hydrogen, alkyl, allyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, and sulfonyl, and further provided that the ring may also contain one or more fused rings, including carbocyclic, heterocyclic, aryl or heteroaryl rings.

As used herein, "alkylene" refers to a straight, branched or cyclic, in certain embodiments straight or branched, divalent aliphatic hydrocarbon group, in one embodiment having from 1 to about 20 carbon atoms, in another embodiment having from 1 to 12 carbons. In a further embodiment alkylene includes lower alkylene. There may be optionally inserted along the alkylene group one or more oxygen, sulphur or substituted or unsubstituted nitrogen atoms, where the nitrogen substituent is alkyl. Alkylene groups include, but are not limited to, methylene (—CH$_2$—), ethylene (—CH$_2$CH$_2$—), propylene (—(CH$_2$)$_3$—), methylenedioxy (—O—CH$_2$—O—) and ethylenedioxy (—O—(CH$_2$)$_2$—O—). The term "lower alkylene" refers to alkylene groups having 1 to 6 carbons. In certain embodiments, alkylene groups are lower alkylene, including alkylene of 1 to 3 carbon atoms.

Methods for preparing Trihydroxy Polyunsaturated Eicosanoids and Analogs

In general, in one aspect, the invention features methods of preparing trihydroxy polyunsaturated eicosanoids, such as 1, as outlined in Scheme 1. This strategy is highly convergent and the two (Z) C=C bonds can be generated at the last step and thereby enhancing the stability and stereochemical integrity of the product. The two (Z) C=C bonds can be formed via selective hydrogenation of the bis-alkynyl precursor 2. The selective hydrogenation can be performed using hydrogen and Lindlar catalyst, or by using activated zinc in the presence of an alcohol such as methanol, or using an aqueous medium. The activated zinc reagent suitable for this process can be prepared from zinc, a copper salt, such as copper acetate and a silver salt, such as silver nitrate according to literature procedures (Boland, W. et al. (1987) *Helv. Chim. Acta* 1987, 70, 1025; Alami, M. et al. (1997) *Tetrahedron Asym.*, 8, 2949; Rodriguez, A. R. et al. (2001) *Tetrahedron Lett.*, 42, 6057).

Compound 2 can be prepared via a palladium-mediated coupling (coupling step a) between intermediates 3 and 4, where X is Br, or I. Compound 4 can be prepared via the olefination of aldehyde 4, which is readily available from protected epoxide 6. Intermediate 3 can be prepared in several different ways, as discussed below, from precursors 7 and 8, while compound 8 can readily prepared from protected epoxide 9.

The invention also provides methods for the preparation of compounds of the general formula 3, which can be used to prepare trihydroxy polyunsaturated eicosanoids or their analogs. Compound 3 can be prepared in several different ways, as outlined in Scheme 2.

According to Method A, compound 3 an be prepared via the addition of an allenyl reagent 11 (M is magnesium, zinc, copper, tin, silicon or boron) to precursor 12, which is readily available via the Pd-coupling between the known bromide 13 and the known alkyne 7.

According to Method B, compound 3 is prepared from precursor 10, which is produced via Pd-mediated coupling (coupling process b) of 7 with intermediate 14. Compound 14, can be prepared via Pd-coupling (coupling process c) between 15 and precursor 16, which can be prepared via the olefination (coupling process d) of aldehyde intermediate 8. Alternatively, compound 14, can be prepared via a Wittig-type reaction (coupling process d) between 20 and aldehyde 8. Compound 14 can also be prepared via silylation of its alkyne precursor 21, which can be formed via addition to the aldehyde 22 (coupling process a).

According to Method C, precursor 10, is formed via the Pd-coupling (coupling process c) between 16 and alkenyl boron compound 17, which is readily available via the Pd-coupling (coupling process c) between alkenyl boron compound 18 and intermediate 7.

Finally, according to Method D, compound 10, is prepared via the alkenylation (coupling process d) of aldehyde intermediate 8 with phosphonate intermediate 19, which is readily available via the Pd-coupling (coupling process b) between the compound 20 with 7.

The present invention involves several distinct building blocks which can be readily prepared as described below.

Scheme 4 shows the synthesis of building blocks of type 4, while Scheme 5 shows the synthesis of building blocks of type 8 and 16. In both cases the stereochemistry of these building blocks is established unambiguously from the starting glycidol and it is retained throughout the synthesis, allowing the synthesis of products with high stereochemical purity.

Scheme 4

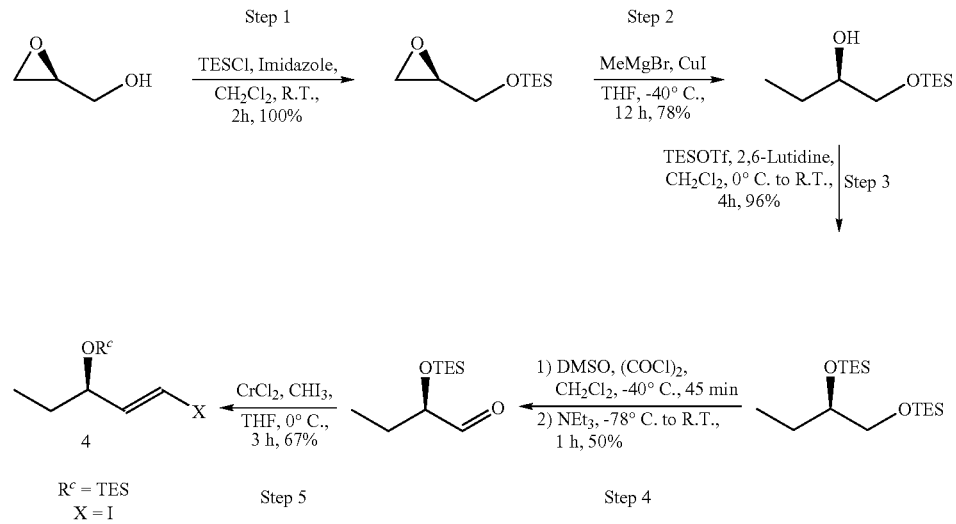

Scheme 5

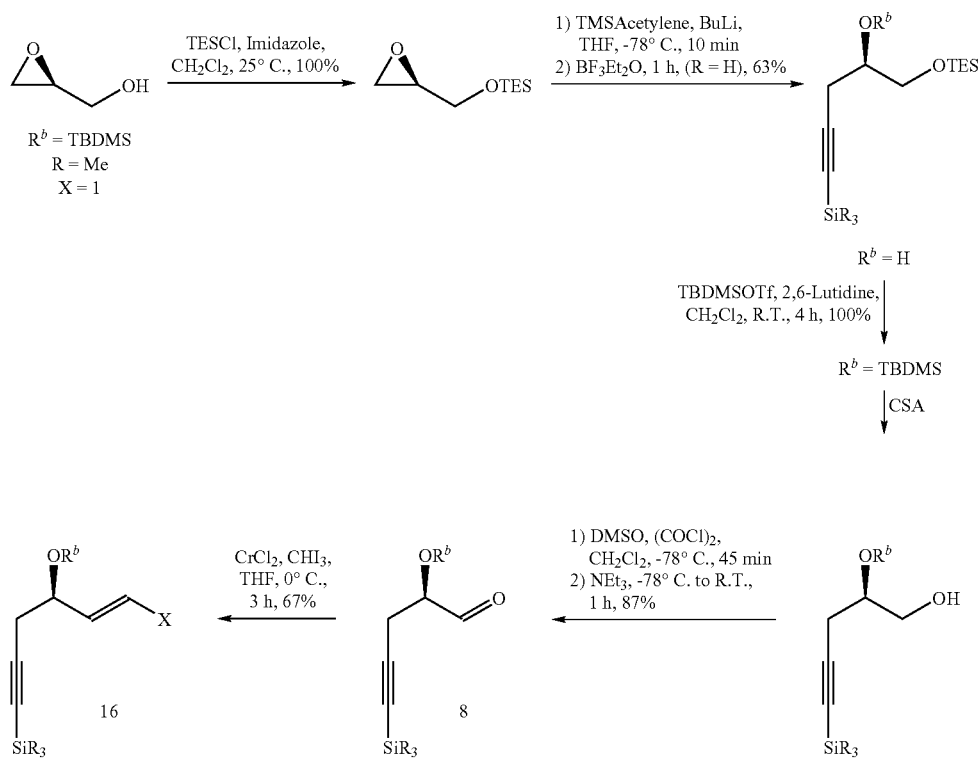

Scheme 6 shows a method for the synthesis of intermediate of type 7 with high stereochemical purity.

dienyl bromide-alcohol to give a product that can be oxidized to an aldehyde. Addition of allenyl boronic acid derivative,

Scheme 6

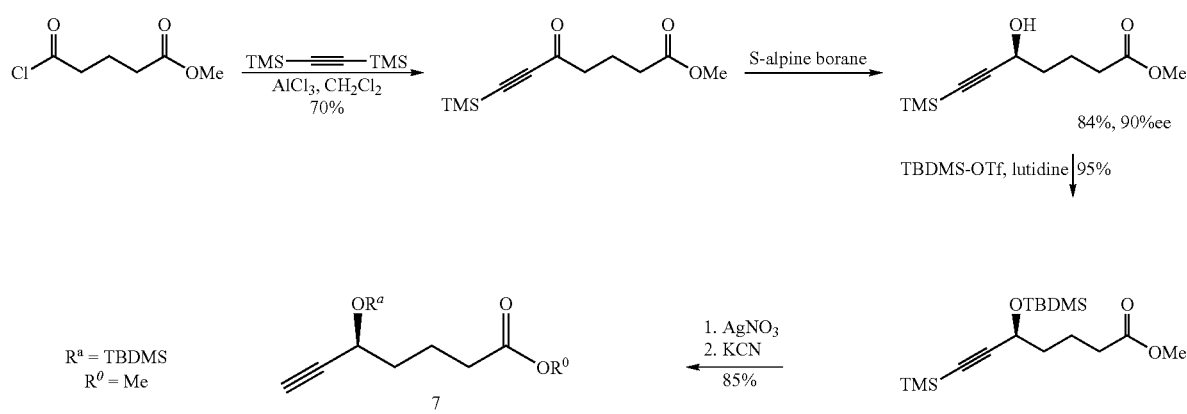

The combination of these building blocks to form key intermediate 3, can be done in a variety of ways. Scheme 7 shows a strategy according to Method A (Scheme 2), whereby the alkyne intermediate of type 7, can be coupled with a dienyl bromide-alcohol to give a product that can be oxidized to an aldehyde. Addition of allenyl boronic acid derivative, according to chemistry reported by Yamamoto (Ikeda, N.; Arai, I.; Yamamoto, H. *J. Am. Chem. Soc.* 1986, 108, 483.) forms the intermediate of type 3, in good overall yield, but with modest stereocontrol.

Scheme 7
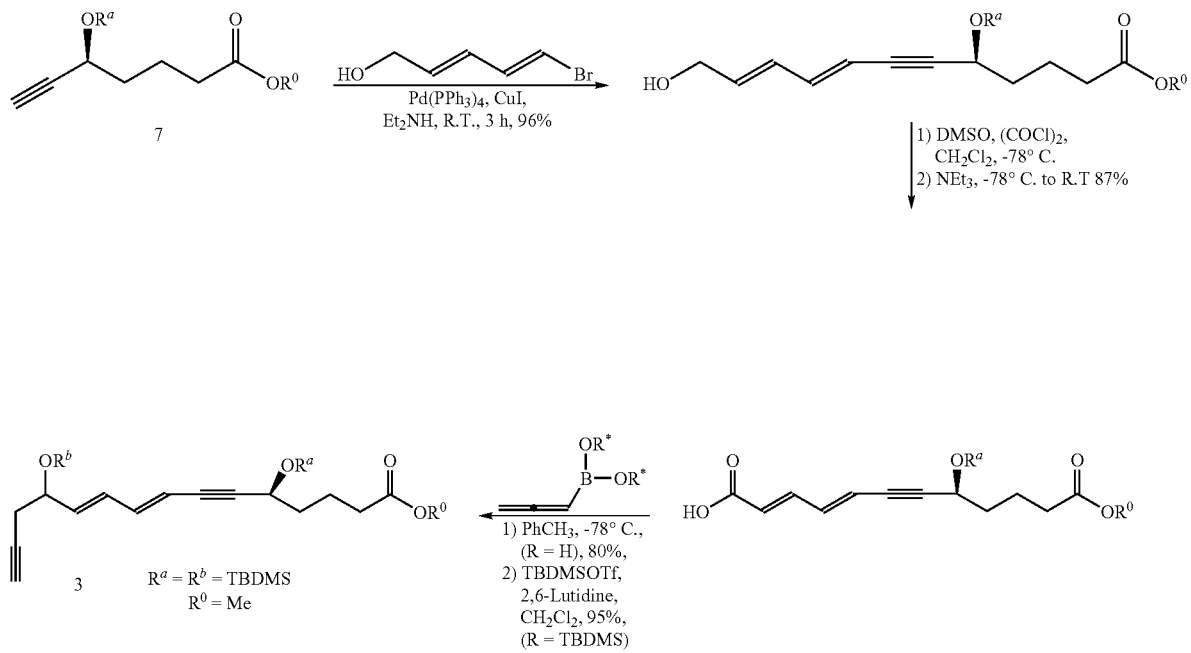
Scheme 8 shows an alternative way to prepare the intermediate of type 3 is via an intermediate of type 10. According to Method B (Scheme 2) Negishi-type coupling of intermediate of type 16 followed by Sonogashira coupling with intermediate of type 7 gives the intermediate of type 10, which can be de-silylated to form the key intermediate of type 3.
Scheme 8
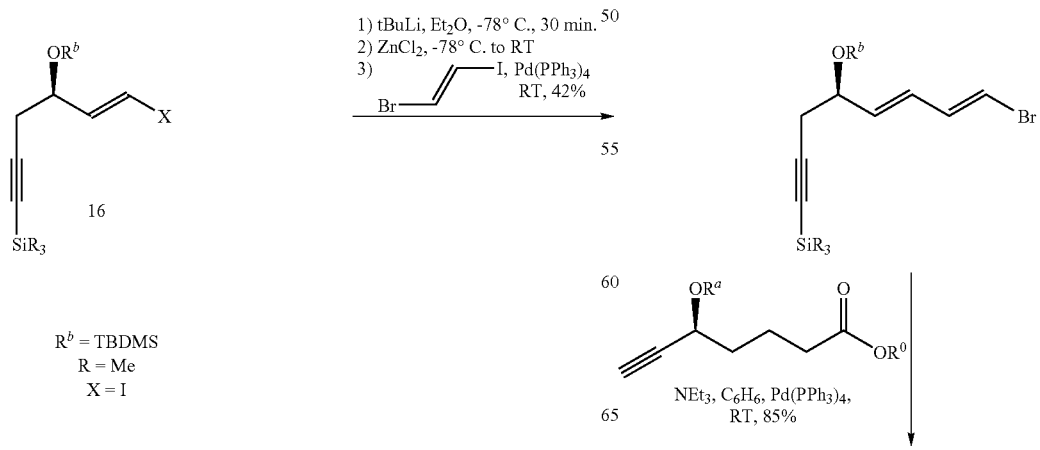

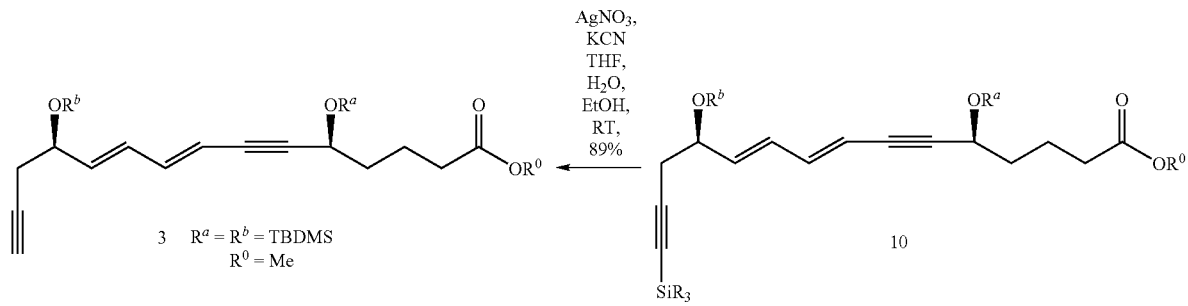

Another approach according to Method C for the preparation of 10, is shown in Scheme 9. Sonogashira coupling, followed by a Suzuki coupling gives the final product. This iterative coupling can be done in a sequential manner and it is possible to do this in one pot.

Scheme 10 shows one of the most effective ways to make intermediates of type 10, which can be produced via Pd-mediated coupling of 7 with intermediate 14. Compound 14 can be prepared via a Wittig-type reaction between phosphonate 20 and aldehyde 8, followed by isomerization to the

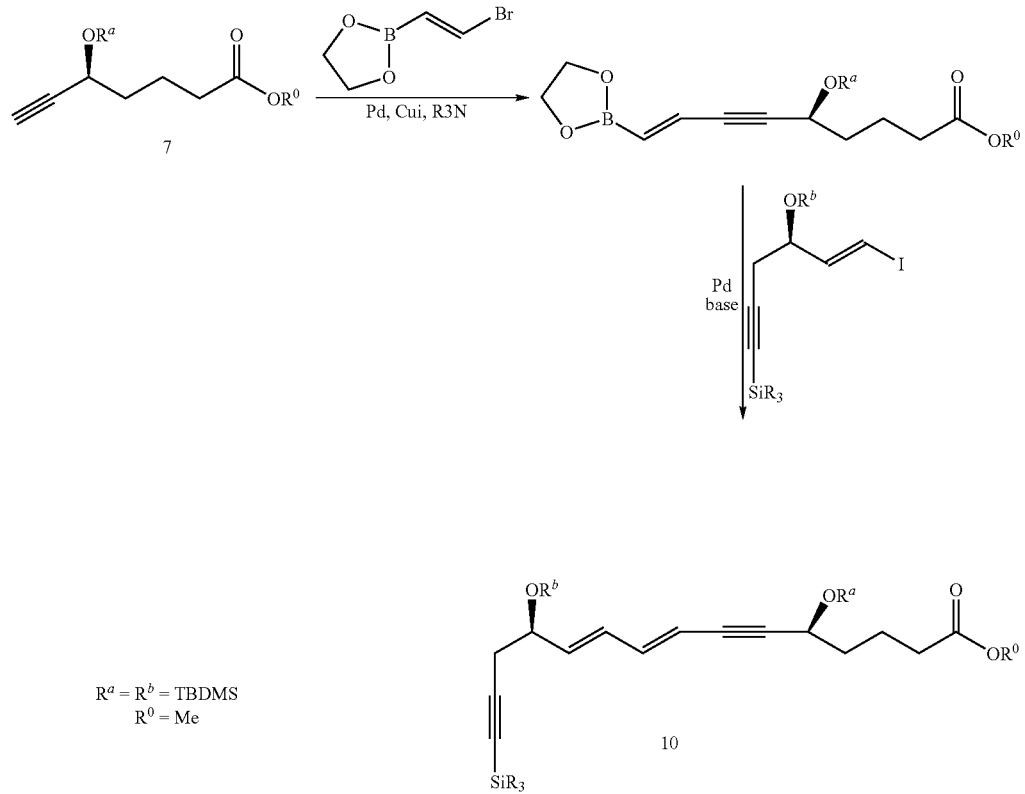

(E,E)-diene. Alternatively, compound 7 can be coupled with 20 via Pd-coupling to form phosphonate 19 which can be used in a Wittig-type reaction with aldehyde 8 followed by isomerization to form 10.

mediates 3 and 4, followed by deprotection gives the bis-alkynyl product of type 2. The final compound of type 1 can be obtained via selective hydrogenation using hydrogen and Lindlar catalyst or alternatively using activated zinc. The

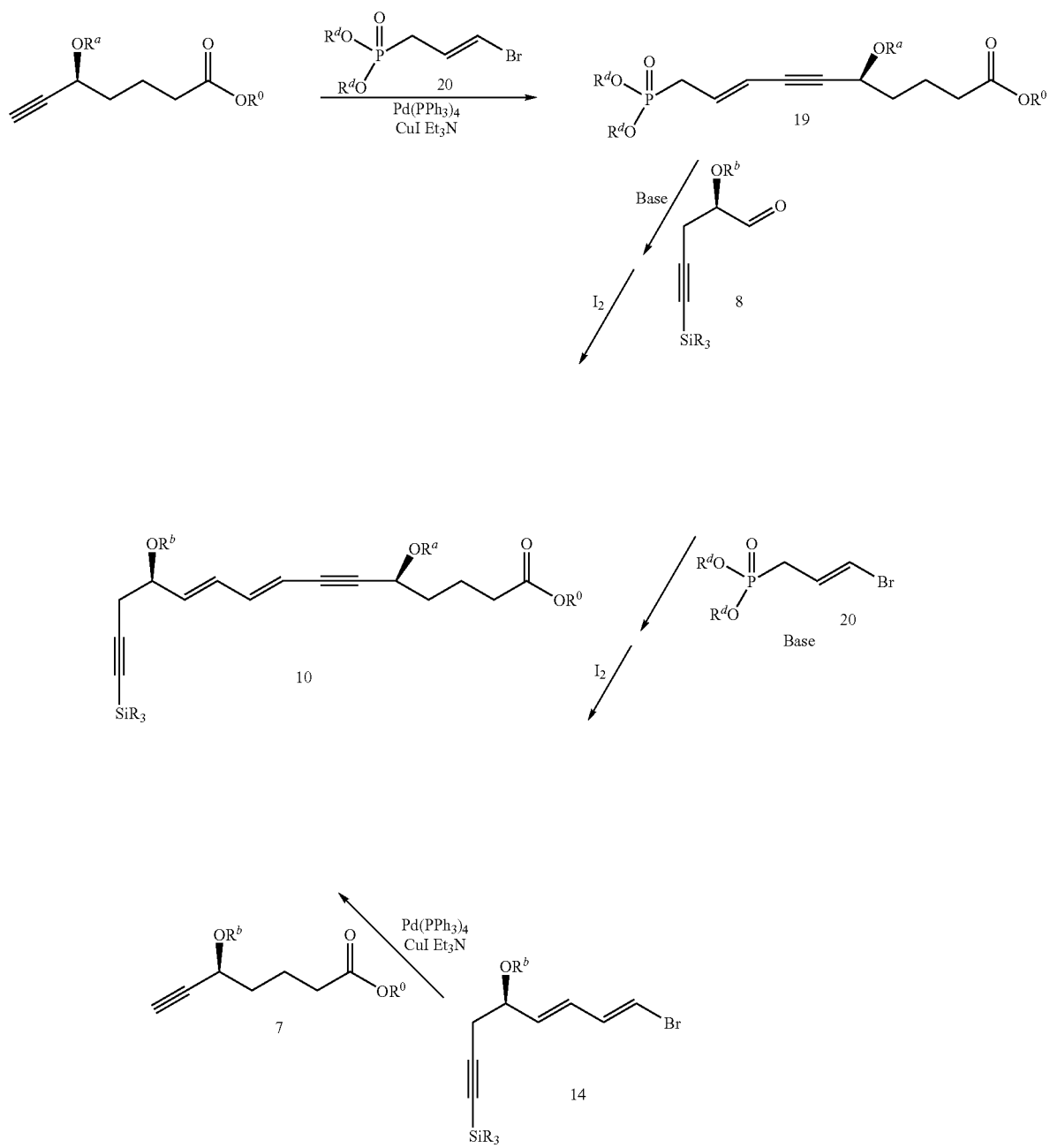

The final assembly of trihydroxy polyunsaturated eicosanoids and their analogs can be done as shown in Scheme 11. Sonogashira-type coupling of the two key interactivated zinc is typically used in methanol or aqueous media and can be prepared from zinc, Cu(OAc)$_2$.H$_2$O and AgNO$_3$ using literature procedures (Boland, W. et al. (1987) *Helv.*

*Chim. Acta* 1987, 70, 1025; Alami, M. et al. (1997) *Tetrahedron Asymmetry*, 8, 2949; Rodriguez, A. R. et al. (2001) *Tetrahedron Lett.*, 42, 6057).

resolvin derivatives. Such isotopically labeled polyunsaturated lipid mediators are useful as spectrometric or molecular probes for the detection and study of the biological actions of

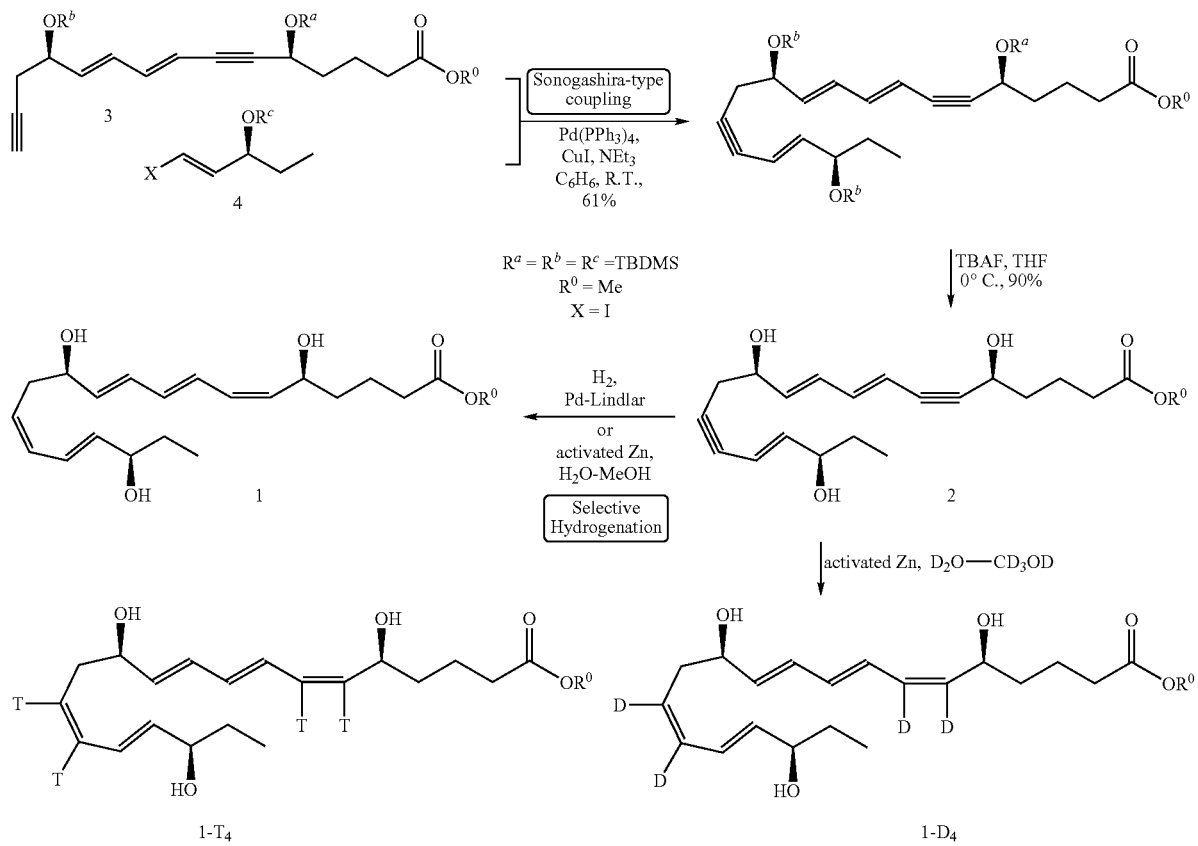

Another embodiment of the present invention involves the preparation of isotopically labeled derivatives of lipid mediators, such as 1 and its analogs, by using activated zinc in the presence of isotopically labeled media, such as isotopically labeled water and isotopically labeled methanol. For example, compound 2 can be converted to the tetra-deuterio derivative 1-$D_4$ by using activated zinc-$D_2O$—$CD_3OD$, while the corresponding tritiated derivative 1-$T_4$ can be prepared similarly from tritiated water. This labeling process, can also be used to prepare other isotopically labeled polyunsaturated lipid mediators, such as lipoxins, leukotrienes and other these molecules. The present synthesis offers major experimental advantages over the prior art. In the general case, outlined below, the present method can be used to prepare a wide range of compounds of the general formulas shown, wherein:

$R^a$ is hydrogen, alkyl, aryl, heteroaryl, acyl, silyl, alkoxyacyl and aminoacyl; and $R_A$ and $R_B$ are independently selected from the group consisting of alkyl, perfluoroalkyl, alkenyl, aryl or heteroaryl.

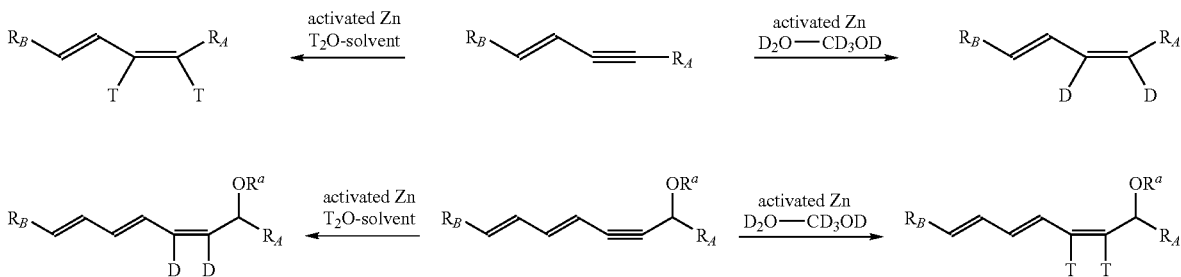

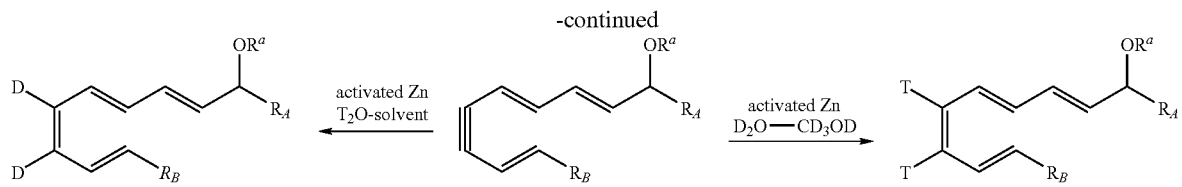

Overall the provided synthetic methodology is highly convergent and allows a number of possible combinations of the key intermediates by using Pd-mediated coupling processes.

The above methodology is highly versatile and it can be readily extended to a variety of analogs of trihydroxy polyunsaturated eicosanoids that have similar frameworks. Thus, in another aspect, the invention features methods for the synthesis of compounds having the general formulas 23 and 24, as outlined in Scheme 3. Compound 23 can be prepared via the selective hydrogenation of compound 24, which can be produced via a Sonogashira-type coupling among compounds 25 and 26:

substituents selected from the group consisting of hydrogen, alkyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, and sulfonyl, and further provided that Y, Z and W can also contain one or more fused carbocyclic, heterocyclic, aryl or heteroaryl rings, and provided that all linkers Y are connected to the adjacent C(R)OR group via a carbon atom;

Scheme 3 wherein:

$R^a$, $R^b$ and $R^c$, are independently selected from the group consisting of hydrogen, alkyl, aryl, heteroaryl, acyl, silyl, alkoxyacyl and aminoacyl;

$R^1$, $R^2$ and $R^3$ are independently selected from the group consisting of hydrogen, alkyl, perfluoroalkyl, aryl and heteroaryl;

Q is selected from the group consisting of:
—C(O)-A, —SO$_2$-A, —PO(OR)-A, where A is hydroxy, alkoxy, aryloxy, amino, alkylamino, dialkylamino, or —OM, where M is a cation selected from the group consisting of ammonium, tetra-alkyl ammonium, Na, K, Mg, and Zn, and R is hydroxyl or alkoxy;

Y, Z and W are linkers independently selected from the group consisting of a ring containing up to 20 atoms and a chain of up to 20 atoms, provided that Y, Z and W can independently include one or more nitrogen, oxygen, sulfur or phosphorous atoms, and further provided that Y, Z and W can independently include one or more X is Cl, Br or I; and G is selected from the group consisting of hydrogen, alkyl, perfluoroalkyl, alkenyl, alkynyl, aryl, heteroaryl, chloro, iodo, bromo, fluoro, hydroxy, alkoxy, aryloxy, carboxy, amino, alkylamino, dialkylamino, acylamino, and carboxamido.

In some embodiments, the invention provides a method for the synthesis of compounds of general formulas 27 and 28 (Scheme 12), wherein:

A is hydroxy, alkoxy, aryloxy, amino, alkylamino, dialkylamino, or —OM, where M is a cation selected from the group consisting of ammonium, tetra-alkyl ammonium, Na, K, Mg, and Zn; and $R^a$, $R^b$ and $R^c$, are independently selected from the group consisting of hydrogen, alkyl, aryl, heteroaryl, acyl, silyl, alkoxyacyl and aminoacyl; and As outlined in Scheme 12, compound 27 can be prepared via the selective hydrogenation of compound 28, which can be performed by treating compound 28 with hydrogen and Lindlar catalyst or by using activated zinc in the presence of an alcohol such as methanol, or using an aqueous medium.

The activated zinc reagent suitable for this process can be prepared from zinc, a copper salt, such as copper acetate and a silver salt, such as silver nitrate.

Compounds of the general formula 28 can be prepared via a Sonogashira-type coupling among a compound of formula 29 and a compound of formula 4, where X is Cl, Br or I. For example compounds 29 and 4 can be converted to 28, upon treatment with a palladium catalyst, such as tetrakis(triphenyl phosphine)palladium, in the presence of a copper salt such as copper(I) iodide, and an amine base such as triethylamine.

Compound 29 can also be prepared via the addition of an allenyl organoboron derivative or other allenyl organometallic derivative 11 to aldehyde 38, which can be prepared form 33.

In compounds shown in Scheme 12,

A is hydroxy, alkoxy, aryloxy, amino, alkylamino, dialkylamino, or —OM, where M is a cation selected from the group consisting of ammonium, tetra-alkyl ammonium, Na, K, Mg, and Zn;

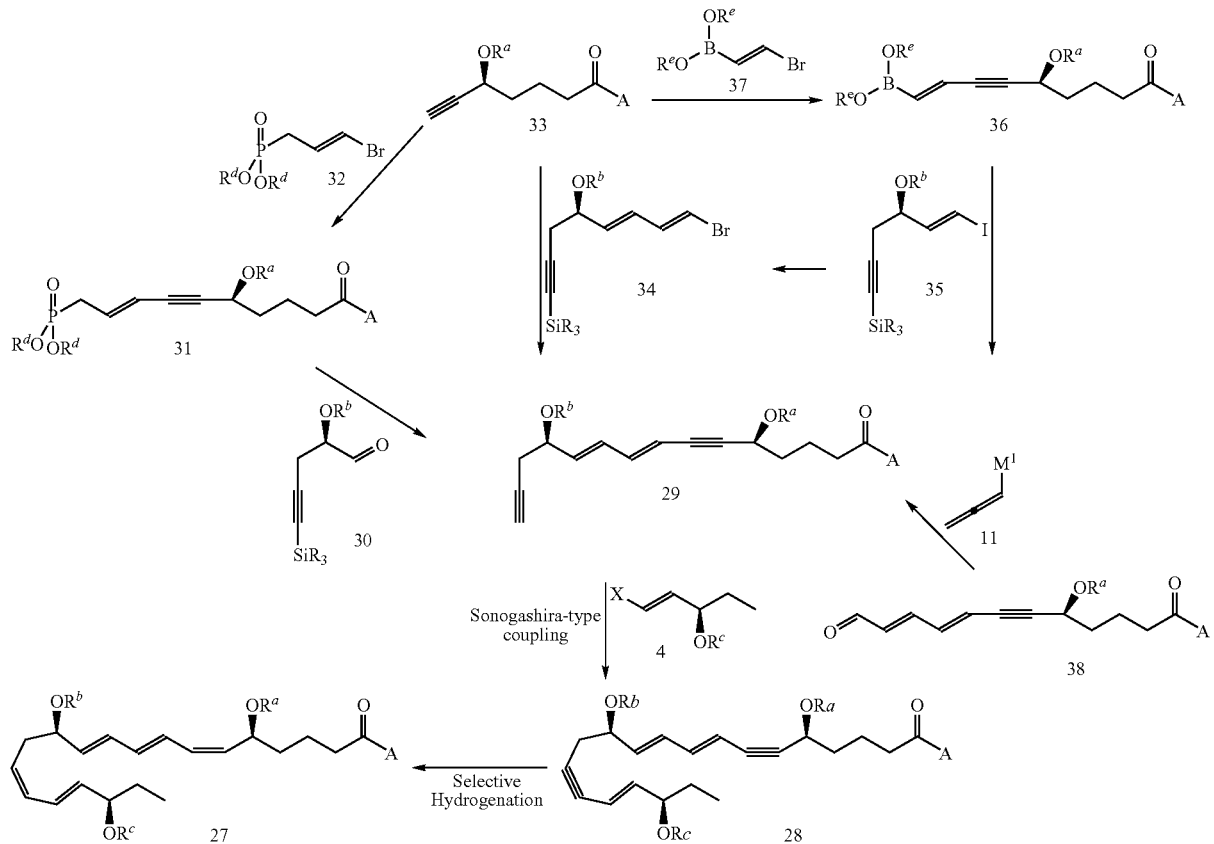

Scheme 12

The invention also provides methods for the preparation of compound of formula 29 or its analogs. Compound 29 can be prepared via several methods which are outlined in Scheme 12. One such method involves the Wittig-type coupling among an aldehyde compound of formula 30 and a phosphonate compound of formula 31, followed by desilylation. Compound 31 can be formed via the Sonogashira-type coupling among compound 32 and alkyne compound 33.

In another embodiment, compound 29 can be prepared via the direct Sonogashira-type coupling among alkyne compound 33 and compound of formula 34. Alternatively, compound 33 can be coupled to compound 37 to form compound 36 which can undergo a Suzuki-type coupling with compound 35 to produce, after desilylation, the key compound 29. Compound of formula 34 can be prepared by several methods, including the Wittig-type coupling between aldehyde 30 and phosphonate 31, and the palladium-mediated homologation of compound 35.

$R^a$ and $R^b$ are independently selected from the group consisting of hydrogen, alkyl, aryl, heteroaryl, acyl, silyl, alkoxyacyl and aminoacyl; and X is Cl, Br or I;

$R^d$ is alkyl or aryl; and $R^e$ is hydrogen, alkyl or aryl; and each of the three R groups in $SiR_3$ is independently selected from a group consisting of alkyl, aryl and alkoxy; and $M^2$ is magnesium zinc, copper, tin, silicon or boron.

Trihydroxy Polyunsaturated Eicosanoid Analogs

The invention also provides compounds and compositions containing synthetic analogs of trihydroxy polyunsaturated eicosanoids that are synthetic derivatives or analogs of compound 1 and exhibit improved chemical and biological properties. The provided compounds include derivatives having the general formulas 27 and 28.

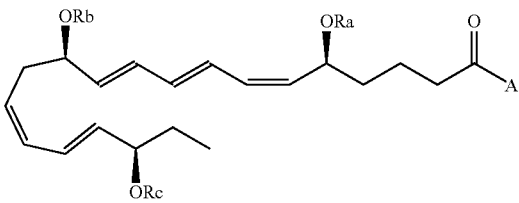

27

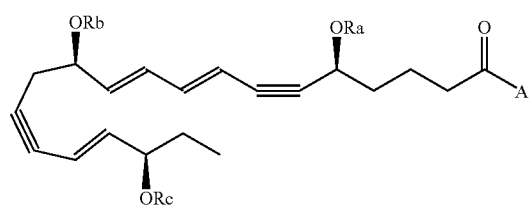

28 wherein:

A is hydroxy, alkoxy, aryloxy, amino, alkylamino, dialkylamino, or —OM, where M is a cation selected from the group consisting of ammonium, tetra-alkyl ammonium, Na, K, Mg, and Zn; and $R^a$, $R^b$ and $R^c$, are independently selected from the group consisting of hydrogen, alkyl, aryl, heteroaryl, acyl, silyl, alkoxyacyl and aminoacyl.

The invention also provides compounds having the general formulas 23 and 24, as well as methods for their preparation and use.

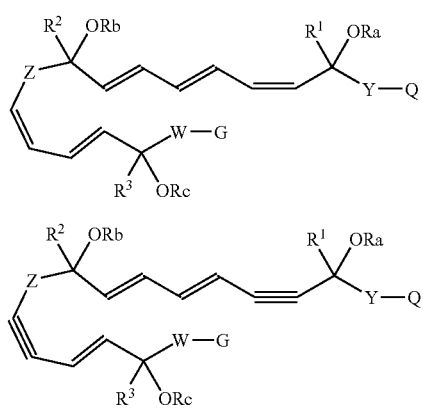

23

24 wherein,

A is hydroxy, alkoxy, aryloxy, amino, alkylamino, dialkylamino, or —OM, where M is a cation selected from a group consisting of ammonium, tetra-alkyl ammonium, Na, K, Mg, or Zn;

$R^a$, $R^b$ and $R^c$, are independently selected from a group that consists of hydrogen, alkyl, aryl, heteroaryl, acyl, silyl, alkoxyacyl or aminoacyl;

$R^1$, $R^2$ and $R^3$ are independently selected from a group that consists of hydrogen, alkyl, perfluoroalkyl, aryl or heteroaryl;

Q is selected from a group that consists of:
—C(O)-A, —SO2-A, —PO(OR)-A, where A is hydroxy, alkoxy, aryloxy, amino, alkylamino, dialkylamino, or —OM, where M is a cation selected from a group consisting of ammonium, tetra-alkyl ammonium, Na, K, Mg, or Zn; and R is hydroxyl or alkoxy;

Y, Z and W are linkers selected from a group consisting of a ring or a chain of up to 20 atoms that may include one or more nitrogen, oxygen, sulfur or phosphorous atoms, provided that linker A can have one or more substituents selected from the group consisting of hydrogen, alkyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, and sulfonyl, and further provided that the linker may also contain one or more fused rings, including carbocyclic, heterocyclic, aryl or heteroaryl rings, provided that all linkers Y are connected to the adjacent C(R)OR group via a carbon atom;

G is selected from a group that consists of hydrogen, alkyl, perfluoroalkyl, alkenyl, alkynyl, aryl, heteroaryl, chloro, iodo, bromo, fluoro, hydroxy, alkoxy, aryloxy, carboxy, amino, alkylamino, dialkylamino, acylamino, and carboxamido.

In certain embodiments, Y, Z and W are each alkylene which can be substituted or unsubstituted. In other embodiments, Y, Z and W are selected from methylene, ethylene and propylene. In other embodiments, Y is propylene. In other embodiments, Z is methylene. In other embodiments, W is ethylene.

Some preferred embodiments of the present invention provide compounds having the general formulas 39 and 40, as well as methods for their preparation and use.

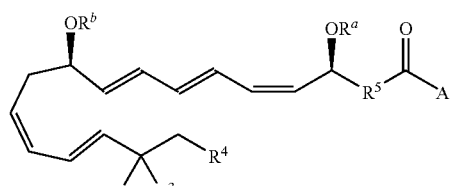

39

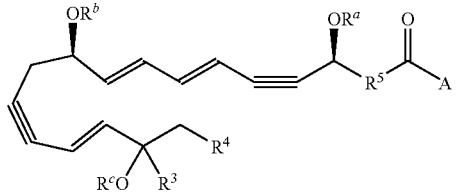

40 wherein:

A is hydroxy, alkoxy, aryloxy, amino, alkylamino, dialkylamino, or —OM, where M is a cation selected from the group consisting of ammonium, tetra-alkyl ammonium, Na, K, Mg, and Zn; and $R^a$, $R^b$ and $R^c$, are independently selected from the group consisting of hydrogen, alkyl, aryl, heteroaryl, acyl, silyl, alkoxyacyl and aminoacyl;

$R^3$ selected from the group consisting of hydrogen, alkyl, perfluoroalkyl, aryl and heteroaryl;

$R^4$ is selected from the group consisting of hydrogen, alkyl, perfluoroalkyl, alkenyl, alkynyl, aryl, heteroaryl, fluoro, hydroxy, alkoxy, aryloxy, $R^5$ is selected from the group consisting of (i)-(iv) as follows:

i) $CH_2CH(R^6)CH_2$, where $R^6$ is hydrogen, alkyl, perfluoroalkyl, aryl, heteroaryl, fluoro, hydroxy or alkoxy;

ii) $CH_2C(R^6R^7)CH_2$, where $R^6$ and $R^7$ are each independently alkyl, perfluoroalkyl, aryl, or fluoro, or $R^6$ and $R^7$ are connected together to form a carbocyclic or heterocyclic ring;

iii) $CH_2OCH_2$, $CH_2C(O)CH_2$, or $CH_2CH_2$; and iv) $R^5$ is a carbocyclic, heterocyclic, aryl or heteroaryl ring; and In certain embodiments, $R^4$ is selected from the group consisting of hydrogen, methyl and trifluoromethyl.

Other preferred embodiments of the present invention provide compounds having the general formulas 41 and 42, as well as methods for their preparation and use.

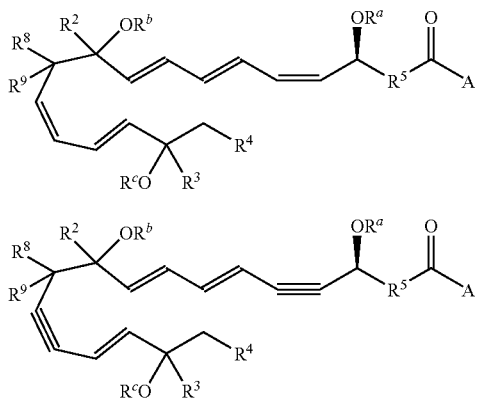

wherein:

A is hydroxy, alkoxy, aryloxy, amino, alkylamino, dialkylamino, or —OM, where M is a cation selected from the group consisting of ammonium, tetra-alkyl ammonium, Na, K, Mg, and Zn; and $R^a$, $R^b$ and $R^c$, are independently selected from the group consisting of hydrogen, alkyl, aryl, heteroaryl, acyl, silyl, alkoxyacyl and aminoacyl;

$R^2$ and $R^3$ are independently selected from the group consisting of hydrogen, alkyl, perfluoroalkyl, aryl and heteroaryl;

$R^4$ is selected from the group consisting of hydrogen, alkyl, perfluoroalkyl, alkenyl, alkynyl, aryl, heteroaryl, fluoro, hydroxy, alkoxy, aryloxy, $R^5$ is selected from the group consisting of (i)-(iv) as follows:

i) $CH_2CH(R^6)CH_2$, where $R^6$ is hydrogen, alkyl, perfluoroalkyl, aryl, heteroaryl, fluoro, hydroxy or alkoxy;

ii) $CH_2C(R^6R^7)CH_2$, where $R^6$ and $R^7$ are each independently alkyl, perfluoroalkyl, aryl, or fluoro, or $R^6$ and $R^7$ are connected together to form a carbocyclic or heterocyclic ring;

iii) $CH_2OCH_2$, $CH_2C(O)CH_2$, or $CH_2CH_2$; and iv) $R^5$ is a carbocyclic, heterocyclic, aryl or heteroaryl ring; and $R^8$ and $R^9$ are independently selected from the group consisting of hydrogen, alkyl, perfluoroalkyl, alkoxy, aryl and heteroaryl, or $R^8$ and $R^9$ are connected together to form a carbocyclic or heterocyclic ring.

In certain embodiments, $R^8$ and $R^9$ are each independently selected from the group consisting of hydrogen, methyl and trifluoromethyl.

In some embodiments the present invention provides compounds of general formulas 29 or 43-47:

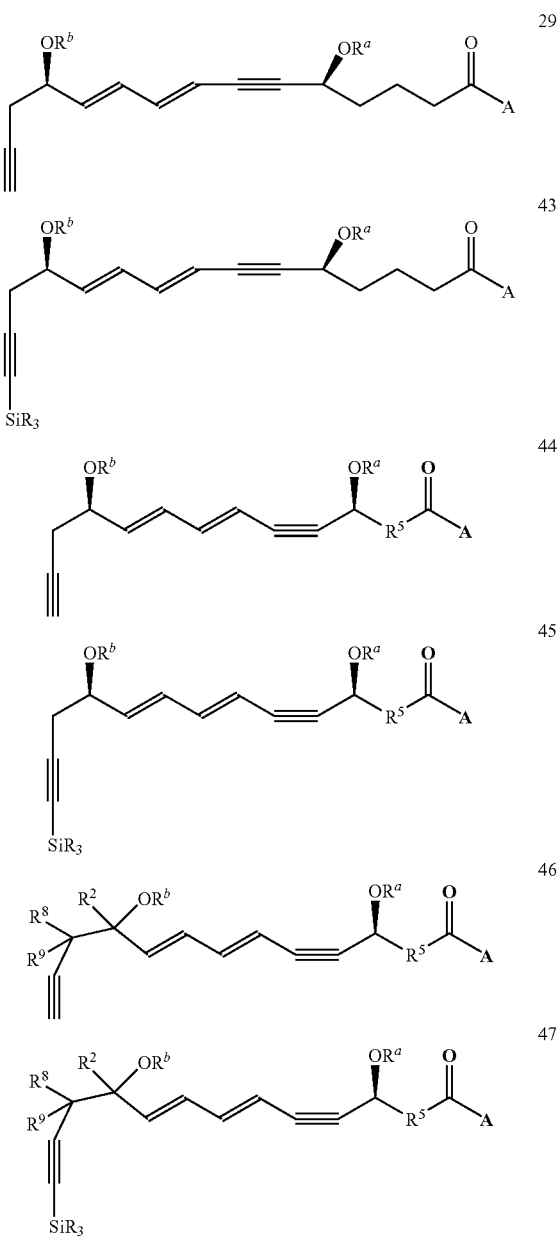

wherein:

A is hydroxy, alkoxy, aryloxy, amino, alkylamino, dialkylamino, or —OM, where M is a cation selected from the group consisting of ammonium, tetra-alkyl ammonium, Na, K, Mg, and Zn; and $R^a$ and $R^b$ are independently selected from the group consisting of hydrogen, alkyl, aryl, heteroaryl, acyl, silyl, alkoxyacyl and aminoacyl;

$R^2$ is hydrogen, alkyl, perfluoroalkyl, aryl and heteroaryl;

$R^5$ is selected from the group consisting of (i)-(iv) as follows:

i) $CH_2CH(R^6)CH_2$, where $R^6$ is hydrogen, alkyl, perfluoroalkyl, aryl, heteroaryl, fluoro, hydroxy or alkoxy;
ii) $CH_2C(R^6R^7)CH_2$, where $R^6$ and $R^7$ are each independently alkyl, perfluoroalkyl, aryl, or fluoro, or $R^6$ and $R^7$ are connected together to form a carbocyclic or heterocyclic ring;
iii) $CH_2OCH_2$, $CH_2C(O)CH_2$, or $CH_2CH_2$; and
iv) $R^5$ is a carbocyclic, heterocyclic, aryl or heteroaryl ring; and $R^8$ and $R^9$ are independently selected from the group consisting of hydrogen, alkyl, perfluoroalkyl, alkoxy, aryl and heteroaryl, or $R^8$ and $R^9$ are connected together to form a carbocyclic or heterocyclic ring; and each of the three R groups in $SiR_3$ is independently selected from a group consisting of alkyl, aryl and alkoxy.

Pharmaceutical Compositions

The compounds of the invention can be incorporated into pharmaceutical compositions suitable for administration. Such compositions typically comprise the active compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable caters include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the treatment methods of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The pharmaceutical compositions can be included in a container, pack, or dispenser together with instructions for administration.

Therapeutic Uses

The compounds of the invention are derivatives or structural analogs of naturally-occurring trihydroxy polyunsaturated eicosanoids that are known to have biological activity against a wide variety of targets, including diseases or conditions associated with inflammation or inflammatory response, autoimmune diseases, rheumatoid arthritis, cardiovascular diseases, or abnormal cell proliferation or cancer. As such, the compounds of the invention are expected to have similar activity against those targets.

Accordingly, in one aspect the invention features methods of ameliorating or treating diseases or conditions associated with inflammation or inflammatory response, involving the administration to a subject of a therapeutically effective amount of a compound or compounds of the invention, such that inflammation or an inflammatory response are significantly reduced or eliminated in the subject. A significant reduction includes the reduction or elimination of a symptom or symptoms associated with the inflammation or inflammatory response.

In another aspect, the invention features methods of ameliorating or treating diseases or conditions associated with abnormal cell proliferation, such as cancer, involving the administration to a subject of an effective amount of a compound or compounds of the invention. In general, an effective amount is an amount sufficient to ensure adequate exposure of a target cell population, such that abnormal cell proliferation is substantially slowed or halted. A target population is a population of cells undergoing abnormal cell proliferation, such as cancerous and/or tumorous growth.

The invention will be further described in the following examples, which are illustrative only, and which are not intended to limit the scope of the invention described in the claims.

EXAMPLES

The invention will be further described in the following examples, which are illustrative only, and which are not intended to limit the scope of the invention described in the claims.

In the following examples, efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric. Starting materials used in these examples are generally either commercially available or can be readily prepared from commercially available reagents by a procedure involving one or more steps.

Example 1

(5S,8E,10E,12R/S)-methyl 5,12-bis(tert-butyldimethylsilyloxy)pentadeca-8,10-dien-6,14-diynoate

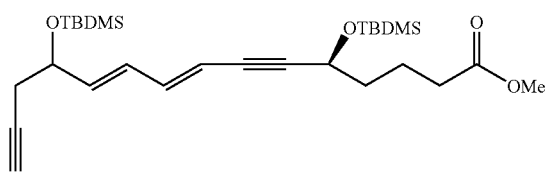

Step 1: To a solution of (2E,4E)-5-bromopenta-2,4-dien-1-ol (0.74 g, 4.51 mmol) in Et$_2$NH (8 ml) was added Pd(PPh$_3$)$_4$ (160 mg, 0.14 mmol) and the solution protected from light was stirred for 45 minutes at room temperature. A small amount of benzene (4 ml) was added to completely dissolve the catalyst. To the resulting homogeneous solution was then added through a cannula a solution of (S)-methyl 5-(tert-butyldimethylsilyloxy)hept-6-ynoate (1.25 g, 4.61 mmol) in Et$_2$NH (8 ml) and CuI (88 mg, 0.46 mmol). The mixture was stirred for 3 h at room temperature and quenched with a saturated aqueous solution of ammonium chloride and extracted with ether. It was then washed with brine, dried and concentrated. Flash column chromatography (silica gel, 20% ethyl acetate/hexanes) afforded the pure product as a colorless liquid (1.52 g, 4.33 mmol, 96% yield). $^1$H NMR (360

MHz, CDCl$_3$): δ 6.61 (dd, J=15.7 Hz and 10.6 Hz, 1H), 6.02 (dd, J=14.8 Hz and 10.9 Hz, 1H), 5.57 (d, J=14.4 Hz), 5.48 (dt, J=15.1 Hz and 5.2 Hz, 1H), 4.54 (m, 1H), 3.75 (s, 2H), 3.30 (s, 3H), 2.14 (t, J=7.0 Hz, 2H), 1.85 (m, 2H), 1.77 (m, 2H), 1.05 (s, 9H), 0.27 (s, 3H), 0.18 (s, 3H). $^{13}$C NMR (62 MHz, CDCl$_3$): δ 141.705, 136.071, 129.466, 111.138, 93.991, 84.393, 63.859, 62.789, 51.161, 38.516, 33.831, 26.244, 21.391, −3.936, −4.648.

Step 2: To a solution of dimethyl sulfoxide (0.66 ml, 8.5 mmol) in CH$_2$Cl$_2$ (40 ml) was added dropwise at −78° C. oxalyl chloride (0.56 ml, 6.4 mmol) and the reaction was stirred at that temperature for 15 minutes. Alcohol from Step 1 (1.5 g, 4.26 mmol) was added via a double-tipped needle and the resulting solution was stirred an additional 45 minutes at −78° C. Triethylamine (2.96 ml, 21.3 mmol) was added slowly to the cloudy white mixture that was allowed to warm up to room temperature and it was then poured into water and extracted with ethyl acetate. The combined extracts were dried and concentrated. Flash column chromatography (silica gel, 5% ethyl acetate/hexanes) afforded the pure product as a colorless liquid (1.31 g, 3.75 mmol, 87% yield). $^1$H NMR (360 MHz, C$_6$D$_6$): δ 9.50 (d, J=8.2 Hz, 1H), 6.31 (dd, J=14.7 Hz and 11.3 Hz, 1H), 6.22 (dd, J=14.6 Hz and 11.2 Hz, 1H), 5.77 (dd, J=14.9 Hz and 8.2 Hz, 1H), 5.59 (d, J=15.9 Hz, 1H), 4.50 (m, 1H), 3.34 (s, 3H), 2.16 (t, J=7.0 Hz, 2H), 1.85 (m, 2H), 1.76 (m, 2H), 1.04 (s, 9H), 0.26 (s, 3H), 0.18 (s, 3H). $^{13}$C NMR (62 MHz, CDCl$_3$): δ 191.944, 172.975, 148.566, 138.933, 133.120, 119.950, 98.691, 83.368, 63.524, 50.987, 38.019, 33.504, 25.921, 21.021, 18.370, −4.320, −4.931.

Step 3: To a solution of the allenyl boronic acid (518 mg, 6.18 mmol) in toluene (20 ml) were added molecular sieves (3.0 g) and diisopropyl-D-tartrate (2.6 ml, 12.36 mmol) and the resulting solution was allowed to stand at room temperature for 24 h with gentle stirring from time to time. The obtained solution of chiral allenyl boronic ester was then cannula to a new flask and cooled at −78° C. At this point a solution of the aldehyde from Step 2 (665 mg, 1.9 mmol) in toluene (10 ml) was added through a double tipped needle and the reaction mixture was stirred at −78° C. for 12 h and then warmed up slowly at room temperature overnight. The resulting solution was then quenched with a diluted solution of HCl, extracted with ether and it was then washed with brine, dried and concentrated. Flash column chromatography (silica gel, 5% ethyl acetate/hexanes) afforded the pure product as a colorless liquid (592 mg, 1.52 mmol, 80% yield). To a solution of the obtained alcohol product (592 mg, 1.52 mmol) in CH$_2$Cl$_2$ (10 ml) were added dropwise at 0° C. 2,6-lutidine (0.40 ml, 3.34 mmol) and tert-butyldimethyl-silyloxy triflate (0.41 ml, 2.28 mmol). The reaction mixture was warmed up to room temperature and stirred for 4 hours. The resulting solution was then poured into a solution of saturated NH$_4$Cl and extracted with diethyl ether. The combined extracts were dried and concentrated. Flash column chromatography (silica gel, 2% ethyl acetate/hexanes) afforded the product as a colorless liquid in 95% yield. $^1$H NMR (250 MHz, CDCl$_3$): δ 6.52 (dd, J=15.5 Hz and 10.9 Hz, 1H), 6.26 (dd, J=15.2 and 11.0 Hz, 1H), 5.85 (dd, J=15.5 Hz and 5.3 Hz, 1H), 5.10 (d, J=16.2 Hz, 1H), 4.51 (t, J=5.6 Hz, 1H), 4.31 (q, J=5.9 Hz, 1H), 3.54 (s, 3H), 2.45 (m, 4H), 1.95 (t, J=1.4 Hz, 1H), 1.82 (m, 4H), 0.97 (s, 18H), 0.18 (s, 3H), 0.12 (s, 3H), 0.07 (s, 3H), 0.05 (s, 3H). $^{13}$C NMR (62 MHz, CDCl$_3$): δ 173.891, 140.738, 137.433, 129.200, 111.125, 93.363, 83.432, 80.947, 71.306, 70.197, 63.012, 51.452, 37.889, 33.516, 28.296, 25.792, 20.566, 18.075, −4.419, −4.578, −4.861, −5.014.

Example 2

(5S,8E,10E,12R)-methyl 5,12-bis(tert-butyldimethylsilyloxy)pentadeca-8,10-dien-6,14-diynoate

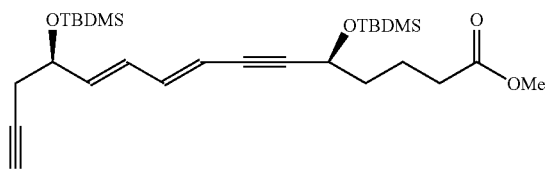

Step 1: To a solution of (R,1E,3E)-1-bromo-5-(tert-butyldimethylsilyloxy)-8-(trimethylsilyl)octa-1,3-dien-7-yne (100 mg, 0.26 mmol) in benzene (1 ml) was added Pd(PPh$_3$)$_4$ (15 mg, 0.013 mmol) and the reaction protected from light was stirred for 45 minutes at room temperature. To the resulting solution was then added through a cannula a solution of(S)-methyl 5-(tert-butyldimethylsilyloxy)hept-6-ynoate (105 mg, 0.39 mmol) in benzene (1 ml), CuI (12 mg, 0.063 mmol) and triethylamine (0.4 g, 4 mmol). The mixture was stirred for 3 hr at room temperature and quenched with a saturated aqueous solution of ammonium chloride and extracted with ether. It was then washed with brine, dried and concentrated. Flash column chromatography (silica gel, 4% diethyl ether/hexanes) afforded the pure product as a colorless liquid (127 mg, 0.22 mmol, 85% yield).

Step 2: To a solution of the product from Step 1 (127 mg, 0.22 mmol) in THF/EtOH (2 ml/1 ml) was added a solution of silver nitrate (106 mg, 0.63 mmol) in water/EtOH (1 ml/1 ml) at 0° C. The resulting yellow solid suspension was allowed to warm to 25° C. and it was then treated with a solution of potassium cyanide (71 mg, 1.09 mmol) in water (1 ml). The product was extracted with ether, washed with brine, dried and concentrated. Flash column chromatography (silica gel, 4% diethyl ether/hexanes) afforded the pure product as a colorless liquid in 89% yield. $^1$H NMR (250 MHz, C$_6$D$_6$): δ 6.58 (dd, J=15.3 Hz and 10.9 Hz, 1H), 6.14 (dd, J=16.0 and 11.0 Hz, 1H), 5.65 (dd, J=16.3 Hz and 6.3 Hz, 1H), 5.56 (d, J=16.0 Hz, 1H), 4.52 (t, J=7.5 Hz, 1H), 4.20 (q, J=6.4 Hz, 1H), 3.34 (s, 3H), 2.20 (m, 4H), 2.12 (t, J=1.4 Hz, 1H), 1.78 (m, 4H), 1.03 (s, 9H), 0.97 (s, 9H), 0.25 (s, 3H), 0.17 (s, 3H), 0.06 (s, 3H), 0.02 (s, 3H); $^{13}$C NMR (62 MHz, CDCl$_3$): δ 173.891, 140.738, 137.433, 129.200, 111.125, 93.363, 83.432, 80.947, 71.306, 70.197, 63.012, 51.452, 37.889, 33.516, 28.296, 25.792, 20.566, 18.075, −4.419, −4.578, −4.861, −5.014.

Example 3

(5S,8E,10E,12R)-methyl 5,12-bis(tert-butyldimethylsilyloxy)pentadeca-8,10-dien-6,14-diynoate

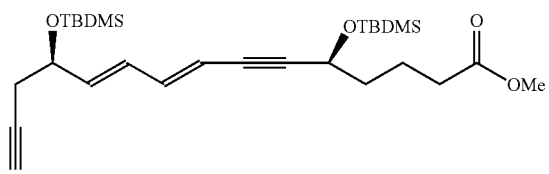

Step 1: A mixture of 3-bromo-propene bromide (0.5 g, 2.5 mmol) and triethylphosphite (neat, 0.83 g, 5 mmol) was heated to 120° C. for 3hr. The excess phosphate was removed under vacuum and used directly in next step.

Step 2: To a solution of the phosphonate product of Step 1 (257 mg, 10 mmol) in 7 ml dry benzene, was added (S)-methyl 5-(tert-butyldimethylsilyloxy)hept-6-ynoate (270 mg, 1.0 mmol), tetrakis(triphenyl phosphine)palladium, (230 mg, 0.2 mmol), copper(I) iodide, (76 mg, 0.4 mmol), and triethylamine (1.01 g, 10 mmol). The mixture was stirred at room temperature, overnight. Removal of the solvent and column chromatography (1% MeOH in diethyl ether) gave the coupled phosphonate product (220 mg, 60%). This compound exhibited satisfactory spectroscopic and analytical data.

Step 3: To a solution of phosphonate from Step 2 (217 mg 0.486 mmol) in 3 ml dry THF, cooled to −78° C. was added 0.51 ml 1M sodium bis(trimethylsilyl)amide (0.51 mmol). The reaction mixture was stirred for 3 min and freshly prepared (R)-2-(tert-butyldimethylsilyloxy)-5-(trimethylsilyl)pent-4-ynal (136 mg, 0.5 mmol) in 2.5 ml THF was added The mixture was stirred at −78° C. for 3 hrs, warmed up to room temperature, and stirred for another 30 mins. Sat. NH4Cl aqueous solution was added, and the mixture was extracted with ether. Removal of the solvent under vacuum and column chromatography (3% ethyl acetate in hexanes) gave 120 mg (43%) of the product.

Step 4: The product of Step 3 was treated similarly to Example 2, Step 2 to give (5S,8E,10E,12R)-methyl 5,12-bis(tert-butyldimethylsilyloxy)pentadeca-8,10-dien-6,14-diynoate.

Example 4

(5S,8E,10E,12R,16E,18R)-methyl 5,12,18-tris(tert-butyldimethylsilyloxy)icosa-8,10,16-trien-6,14-diynoate

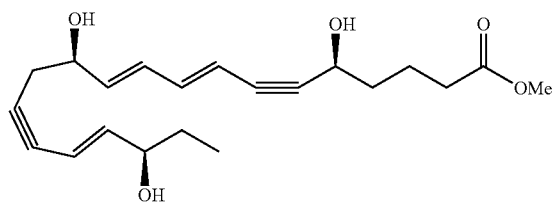

Sonogashira coupling between (R,E)-tert-butyl(1-iodo-pent-1-en-3-yloxy)dimethylsilane and (5S,8E,10E,12R)-methyl 5,12-bis(tert-butyldimethylsilyloxy)pentadeca-8,10-dien-6,14-diynoate (the product of Example 2 or Example 3), using a procedure analogous to that of Example 2, Step 1 gave the product in 80% yield. $^1$H NMR (500 MHz, C$_6$D$_6$): δ 6.59 (dd, J=15.2 Hz and 10.9 Hz, 1H), 6.24 (dd, J=15.2 and 11.0 Hz, 1H), 6.14 (dd, J=15.5 Hz and 5.3 Hz, 1H), 5.86 (d, J=15.4 Hz, 1H), 5.67 (dd, J=14.8 Hz and 5.6 Hz, 1H), 5.59 (d, J=15.5 Hz, 1H), 4.54 (t, J=5.7 Hz, 1H), 4.24 (q, J=5.9 Hz, 1H), 3.94 (q, J=5.6 Hz, 1H), 3.35 (s, 3H), 2.46 (m, 2H), 2.17 (t, J=7.1 Hz, 2H), 1.84 (m, 4H), 1.44 (m, 2H), 1.04 (s, 9H), 1.02 (s, 9H), 1.00 (s, 9H), 0.86 (t, J=7.5 Hz, 3H), 0.28 (s, 3H), 0.19 (s, 3H), 0.14 (s, 3H), 0.08 (s, 3H), 0.07 (s, 3H), 0.05 (s, 3H). $^{13}$C NMR (125 MHz, C$_6$D$_6$): δ 173.131, 145.665, 141.248, 138.411, 129.420, 111.518, 109.904, 93.989, 87.526, 84.119, 81.048, 73.998, 72.025, 63.570, 50.913, 38.321, 33.587, 31.253, 29.235, 26.014, 21.163, 18.413, 9.221, −4.207, −4.421, −4.603, −4.621, −4.772, −5.094.

Example 5

(5S,8E,10E,12R,16E,18R)-methyl 5,12,18-trihydroxyicosa-8,10,16-trien-6,14-diynoate

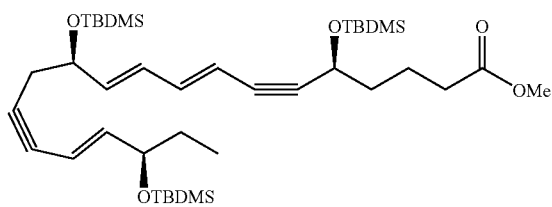

A solution of the product of Example 4 (40 mg, 0.065 mmol) in THF (1 ml) was treated with 1.0 M TBAF (0.32 ml, 0.32 mmol) at 0° C. The reaction was stirred for 3 h and then poured into water and extracted with ether. The ether extracts were washed with brine, dried and concentrated. The ethereal solution was then treated with an excess of freshly prepared diazomethane in ether to convert the free acid to the product. Flash column chromatography (silica gel, 4% MeOH/CH$_2$Cl$_2$) afforded the pure product in 90% yield. $^1$H NMR (500 MHz, C$_6$D$_6$): δ 6.55 (dd, J=15.5 Hz and 10.9 Hz, 1H), 6.16 (dd, J=15.2 Hz and 11.0 Hz, 1H), 6.05 (dd, J=15.5 Hz and 5.3 Hz, 1H), 5.70 (d, J=16.2 Hz, 1H), 5.61 (dd, J=14.6 Hz and 5.5 Hz, 1H), 5.58 (d, J=14.7 Hz, 1H), 4.28 (t, J=5.8 Hz, 1H), 4.06 (dd, J=11.2 Hz and 5.3 Hz, 1H), 3.65 (dd, J=1.0 Hz and 6.7 Hz, 1H), 3.30 (s, 3H), 2.36 (m, 2H), 2.06 (t, J=6.9 Hz, 2H), 1.72 (m, 2H), 1.59 (m, 2H), 1.27 (m, 2H), 0.74 (t, J=7.4 Hz, 3H). $^{13}$C NMR (125 MHz, C$_6$D$_6$): δ 173.819, 145.219, 141.143, 136.647, 130.007, 111.340, 109.915, 92.672, 85.857, 84.082, 81.330, 73.505, 70.225, 62.533, 51.488, 37.097, 33.599, 29.912, 28.658, 20.615, 9.451. HPLC: Beckman Ultrasphere reverse phase column (30% water in MeOH, 3.8 ml/min, 252 bar): elution time=5.41 min.

Example 6

(5S,6Z,8E,10E,12R,14Z,16E,18R)-methyl 5,12,18-trihydroxyicosa-6,8,10,14,16-pentaenoate or resolvin E1 methyl ester

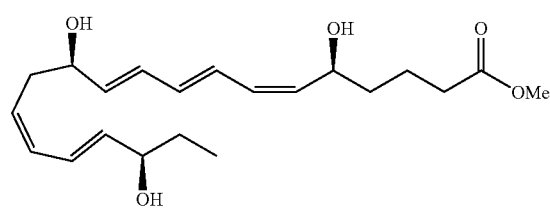

To a solution of the bis-acetylenic product from Example 5 (7.7 mg, 0.021 mmol) in dichloromethane (4 ml) was added Lindlar catalyst (1.5 mg, 20% by weight), quinoline (4 µl), and the reaction mixture was stirred under the static atmosphere of hydrogen. Samples were taken every 20 minutes for HPLC analysis (30% water in MeOH), and the reaction was stopped at 60% conversion. The resulting solution was filtrated over a pad of celite and separated by HPLC (45% water in MeOH) affording the pure product in 60% yield. ¹H NMR (500 MHz, C₆D₆): δ 6.54 (dd, J=14.8 Hz and 11.5 Hz, 1H), 6.49 (dd, J=14.9 Hz and 11.7 Hz, 1H), 6.26 (dd, J=16.0 Hz and 10.5 Hz, 1H), 6.11 (t, J=9.2 Hz, 1H), 6.09 (dd, J=14.7 Hz and 11.1 Hz, 1H), 5.95 15 (t, J=11.0 Hz, 1H), 5.60 (dd, J=15.4 Hz and 6.4 Hz, 1H), 5.56 (dd, J=14.9 Hz and 6.0 Hz, 1H), 5.42 (dt, J=10.8 Hz and 8.1 Hz, 1H), 5.30 (t, J=10.6 Hz, 1H), 4.38 (q, J=7.8 Hz, 1H), 4.03 (q, J=6.6 Hz, 1H), 3.83 (q, J=6.6 Hz, 1H), 3.30 (s, 3H), 2.2-2.4 (m, 4H), 2.08 (t, J=6.9 Hz, 2H), 1.6-1.7 (m, 2H), 1.3-1.5 (m, 2H), 0.85 (t, J=6.7 Hz, 3H). ¹³C NMR (125 MHz, C₆D₆): δ 177.135, 137.855, 137.106, 134.923, 134.057, 131.093, 130.273, 129.637, 128.428, 126.868, 125.269, 73.554, 71.747, 67.609, 37.123, 36.223, 33.835, 30.576, 21.165, 9.867. HPLC: Beckman Ultrasphere reverse phase column (30% water in MeOH, 3.8 ml/min, 254 bar): elution time=8.43 min.

Example 7

(5S,6Z,8E,10E,12R,14Z,16E,18R)-Methyl 6,7,14,15-tetradeuterio-5,12,18-trihydroxyicosa-6,8,10,14,16-pentaenoate

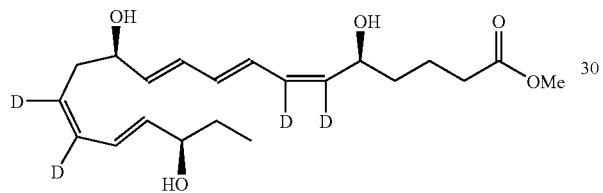

Step 1: To zinc dust (<10 micron, 98+%, Aldrich, 20,998-8) that was weighed under nitrogen, is added deuterated water ((D₂O, 3 ml), which was previously degassed with bubbling nitrogen for 20 minutes. After stirring for 15 mm copper(II) acetate monohydrate (Ac₂Cu.H₂O, 98+%, Aldrich, 6046-93-1, 50 mg) was added and the mixture was stirred for another 20 mm. To the stirred mixture is added slowly silver (I) nitrate, (AgNO₃, 99+%, Aldrich, 20,913-9, 50 mg). The mixture was stirred for another 30 mm and the precipitate was collected by filtration and rinsed with deuterated water (2×3 ml), acetone (2×3 ml), and ether (2×3 ml). The precipitate was mixed with 2.5 ml of a 4:1 mixture by volume of deuterated water:dioxane (1,4-dioxane, anhydrous, 99.8+%, Aldrich, 296309-1L).

Step 2: The Zn—Cu—Ag reagent prepared according to Step 1 was added to a solution of (5S,8E,10E,12R,16E,18R)-methyl 5,12,18-trihydroxyicosa-8,10,16-trien-6,14-diynoate from Example 5, (0.5 mg) in dioxane (0.5 ml) and the mixture was stirred at 40° C. for 24 hr. The mixture is then filtered through a glass fritted funnel, the filtrate is evaporated and the crude product is purified by HPLC to give (5S,6Z,8E,10E,12R,14Z,16E,18R)-Methyl 6,7,14,15-tetradeuterio-5,12,18-trihydroxyicosa-6,8,10,14,16-pentaenoate. This compound gave satisfactory spectra.

A number of embodiments of the invention have been described. Nevertheless, it will be understood that various modifications may be made without departing from the spirit and scope of the invention. Accordingly, other embodiments are within the scope of the following claims.

What is claimed is:

1. A compound having the formula 23,

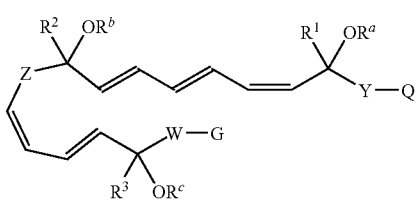

wherein:

Rᵃ, Rᵇ and Rᶜ, are independently selected from the group consisting of hydrogen, alkyl, aryl, heteroaryl, acyl, silyl, alkoxyacyl and aminoacyl;

R¹, R² and R³ are independently selected from the group consisting of hydrogen, alkyl, perfluoroalkyl, aryl and heteroaryl;

Q is selected from the group consisting of:
—C(O)-A, —SO₂-A, —PO(OR)-A, where A is hydroxyl, alkoxy, aryloxy, amino, alkylamino, dialkylamino, or —OM, where M is a cation selected from the group consisting of ammonium, tetra-alkyl ammonium, Na, K, Mg, and Zn, and R is hydroxyl or alkoxy;

Y, Z and W are linkers independently selected from the group consisting of a ring containing up to 20 atoms and a chain of up to 20 atoms, provided that Y, Z and W can independently include one or more nitrogen, oxygen, sulfur or phosphorous atoms, and further provided that Y, Z and W can independently include one or more substituents selected from the group consisting of hydrogen, alkyl, alkenyl, alkynyl, aryl, heteroaryl, chloro, iodo, bromo, fluoro, hydroxyl, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, and sulfonyl, and further provided that Y, Z and W can also contain one or more fused carbocyclic, heterocyclic, aryl or heteroaryl rings, and provided that all linkers Y are connected to the adjacent C(R)OR group via a carbon atom; and G is selected from the group consisting of hydrogen, alkyl, perfluoroalkyl, alkenyl, alkynyl, aryl, heteroaryl, chloro, iodo, bromo, fluoro, hydroxyl, alkoxy, aryloxy, carboxy, amino, alkylamino, dialkylamino, acylamino, and carboxamido.

2. A pharmaceutical composition, comprising a compound according to claim 1; and a pharmaceutically acceptable carrier.

3. A compound having a formula 39 or a formula 41,

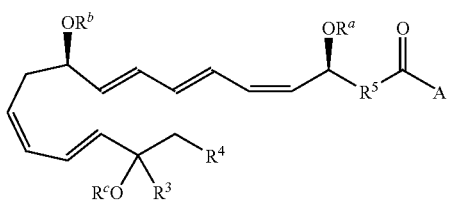

-continued

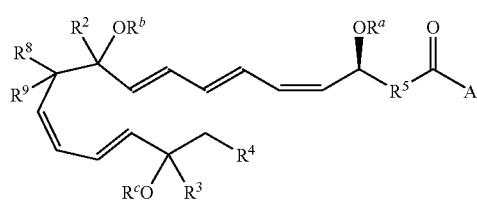

wherein:
A is hydroxyl, alkoxy, aryloxy, amino, alkylamino, dialkylamino, or —OM, where M is a cation selected from the group consisting of ammonium, tetra-alkyl ammonium, Na, K, Mg, and Zn; and $R^a$, $R^b$ and $R^c$, are independently selected from the group consisting of hydrogen, alkyl, aryl, heteroaryl, acyl, silyl, alkoxyacyl and aminoacyl;

$R^2$ and $R^3$ are independently selected from the group consisting of hydrogen, alkyl, perfluoroalkyl, aryl and heteroaryl;

$R^4$ is selected from the group consisting of hydrogen, alkyl, perfluoroalkyl, alkenyl, alkynyl, aryl, heteroaryl, fluoro, hydroxyl, alkoxy, aryloxy, $R^5$ is selected from the group consisting of (i)-(iv) as follows:
  i) $CH_2CH(R^6)CH_2$, where $R^6$ is hydrogen, alkyl, perfluoroalkyl, aryl, heteroaryl, fluoro, hydroxyl or alkoxy;
  ii) $CH_2C(R^6R^7)CH_2$, where $R^6$ and $R^7$ are each independently alkyl, perfluoroalkyl, aryl, or fluoro, or $R^6$ and $R^7$ are connected together to form a carbocyclic or heterocyclic ring;
  iii) $CH_2OCH_2$, $CH_2C(O)CH_2$, or $CH_2CH_2$; and
  iv) $R^5$ is a carbocyclic, heterocyclic, aryl or heteroaryl ring; and $R^8$ and $R^9$ are independently selected from the group consisting of hydrogen, alkyl, perfluoroalkyl, alkoxy, aryl and heteroaryl, or $R^8$ and $R^9$ are connected together to form a carbocyclic or heterocyclic ring; and provided that the compound of formula 39 or formula 41 is not a compound of formula 27,

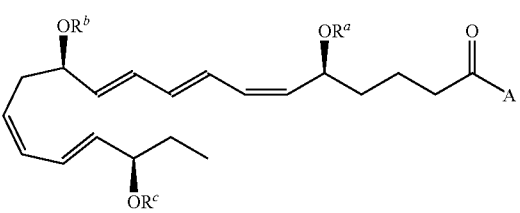

wherein:
A is hydroxyl, alkoxy, aryloxy, amino, alkylamino, dialkylamino, or —OM, where M is a cation selected from the group consisting of ammonium, tetra-alkyl ammonium, Na, K, Mg, and Zn;

$R^a$, $R^b$ and $R^c$, are independently selected from the group consisting of hydrogen, alkyl, aryl, heteroaryl, acyl, silyl, alkoxyacyl and aminoacyl.

4. A pharmaceutical composition, comprising a compound according to claim 3; and a pharmaceutically acceptable carrier.

5. A compound having a formula 40 or a formula 42,

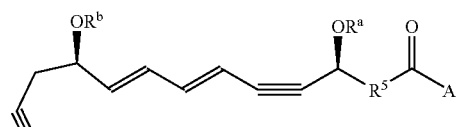

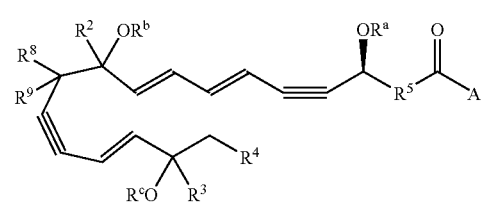

wherein:
A is hydroxyl, alkoxy, aryloxy, amino, alkylamino, dialkylamino, or —OM, where M is a cation selected from the group consisting of ammonium, tetra-alkyl ammonium, Na, K, Mg, and Zn; and $R^a$, $R^b$ and $R^c$, are independently selected from the group consisting of hydrogen, alkyl, aryl, heteroaryl, acyl, silyl, alkoxyacyl and aminoacyl;

$R^2$ and $R^3$ are independently selected from the group consisting of hydrogen, alkyl, perfluoroalkyl, aryl and heteroaryl;

$R^4$ is selected from the group consisting of hydrogen, alkyl, perfluoroalkyl, alkenyl, alkynyl, aryl, heteroaryl, fluoro, hydroxyl, alkoxy, aryloxy, $R^5$ is selected from the group consisting of (i)-(iv) as follows:
  i) $CH_2CH(R^6)CH_2$, where $R^6$ is hydrogen, alkyl, perfluoroalkyl, aryl, heteroaryl, fluoro, hydroxyl or alkoxy;
  ii) $CH_2C(R^6R^7)CH_2$, where $R^6$ and $R^7$ are each independently alkyl, perfluoroalkyl, aryl, or fluoro, or $R^6$ and $R^7$ are connected together to form a carbocyclic or heterocyclic ring;
  iii) $CH_2OCH_2$, $CH_2C(O)CH_2$, or $CH_2CH_2$; and
  iv) $R^5$ is a carbocyclic, heterocyclic, aryl or heteroaryl ring; and $R^8$ and $R^9$ are independently selected from the group consisting of hydrogen, alkyl, perfluoroalkyl, alkoxy, aryl and heteroaryl, or $R^8$ and $R^9$ are connected together to form a carbocyclic or heterocyclic ring.

6. A pharmaceutical composition, comprising a compound according to claim 5; and a pharmaceutically acceptable carrier.

7. A compound selected from a group consisting of compounds having the general formulas 29 or 43-47:

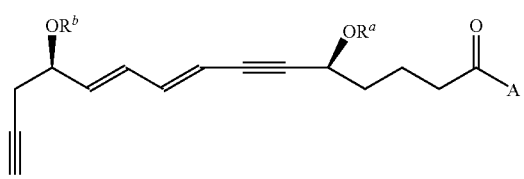

-continued

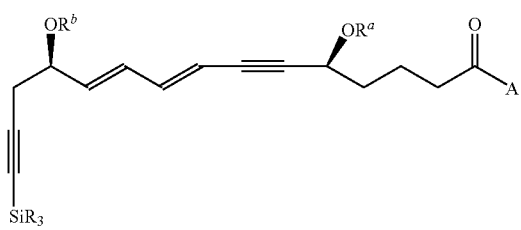
43

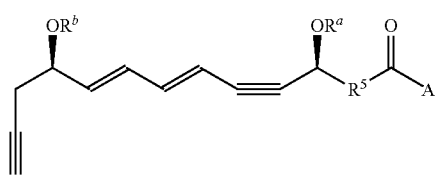
44

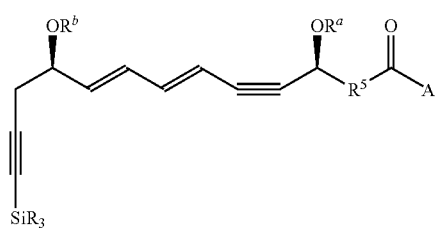
45

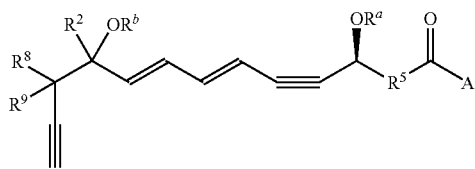
46

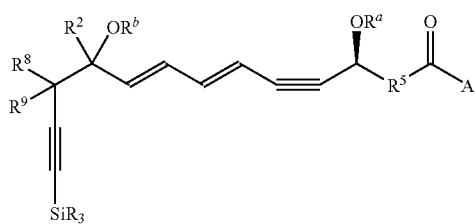
47 wherein:

A is hydroxyl, alkoxy, aryloxy, amino, alkylamino, dialkylamino, or —OM, where M is a cation selected from the group consisting of ammonium, tetra-alkyl ammonium, Na, K, Mg, and Zn; and $R^a$ and $R^b$ are independently selected from the group consisting of hydrogen, alkyl, aryl, heteroaryl, acyl, silyl, alkoxyacyl and aminoacyl;

$R^2$ is hydrogen, alkyl, perfluoroalkyl, aryl and heteroaryl;

$R^5$ is selected from the group consisting of (i)-(iv) as follows:
  i) $CH_2CH(R^6)CH_2$, where $R^6$ is hydrogen, alkyl, perfluoroalkyl, aryl, heteroaryl, fluoro, hydroxyl or alkoxy;
  ii) $CH_2C(R^6R^7)CH_2$, where $R^6$ and $R^7$ are each independently alkyl, perfluoroalkyl, aryl, or fluoro, or $R^6$ and $R^7$ are connected together to form a carbocyclic or heterocyclic ring;
  iii) $CH_2OCH_2$, $CH_2C(O)CH_2$, or $CH_2CH_2$; and
  iv) $R^5$ is a carbocyclic, heterocyclic, aryl or heteroaryl ring; and $R^8$ and $R^9$ are independently selected from the group consisting of hydrogen, alkyl, perfluoroalkyl, alkoxy, aryl and heteroaryl, or $R^8$ and $R^9$ connected together to form a carbocyclic or heterocyclic ring; and each of the three R groups in $SiR_3$ is independently selected from a group consisting of alkyl, aryl and alkoxy.

8. A compound having the general formula 3:

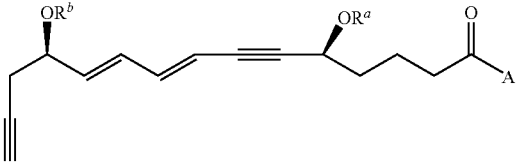
3 wherein $R^o$ is methyl; and $R^a$ and $R^b$ are independently selected from the group consisting of hydrogen, alkyl, aryl, heteroaryl, acyl, silyl, alkoxyacyl and aminoacyl.

9. A compound having the general formula 29:

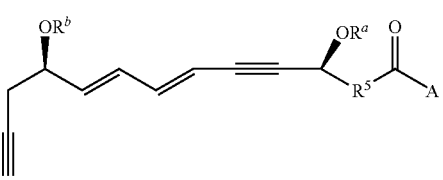
29 wherein:

A is hydroxyl, alkoxy, aryloxy, amino, alkylamino, dialkylamino, or —OM, where M is a cation selected from the group consisting of ammonium, tetra-alkyl ammonium, Na, K, Mg, and Zn; and $R^a$ and $R^b$ are independently selected from the group consisting of hydrogen, alkyl, aryl, heteroaryl, acyl, silyl, alkoxyacyl and aminoacyl.

10. A compound having the general formula 44:

44 wherein:

A is hydroxyl, alkoxy, aryloxy, amino, alkylamino, dialkylamino, or —OM, where M is a cation selected from the group consisting of ammonium, tetra-alkyl ammonium, Na, K, Mg, and Zn;

$R^a$ and $R^b$ are independently selected from the group consisting of hydrogen, alkyl, aryl, heteroaryl, acyl, silyl, alkoxyacyl and aminoacyl; and $R^5$ is selected from the group consisting of (i)-(iv) as follows:

i) CH$_2$CH(R$^6$)CH$_2$, where R$^6$ is hydrogen, alkyl, perfluoroalkyl, aryl, heteroaryl, fluoro, hydroxyl or alkoxy;
ii) CH$_2$C(R$^6$R$^7$)CH$_2$, where R$^6$ and R$^7$ are each independently alkyl, perfluoroalkyl, aryl, or fluoro, or R$^6$ and R$^7$ are connected together to form a carbocyclic or heterocyclic ring;
iii) CH$_2$OCH$_2$, CH$_2$C(O)CH$_2$, or CH$_2$CH$_2$; and
iv) R$^5$ is a carbocyclic, heterocyclic, aryl or heteroaryl ring.

11. A compound having the general formula 46

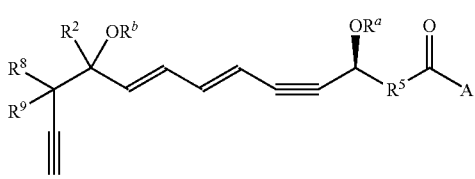

46 wherein:
A is hydroxyl, alkoxy, aryloxy, amino, alkylamino, dialkylamino, or —OM, where M is a cation selected from the group consisting of ammonium, tetra-alkyl ammonium, Na, K, Mg, and Zn; and
R$^a$ and R$^b$ are independently selected from the group consisting of hydrogen, alkyl, aryl, heteroaryl, acyl, silyl, alkoxyacyl and aminoacyl;
R$^2$ is hydrogen, alkyl, perfluoroalkyl, aryl or heteroaryl;
R$^5$ is selected from the group consisting of (i)-(iv) as follows:
i) CH$_2$CH(R$^6$)CH$_2$, where R$^6$ is hydrogen, alkyl, perfluoroalkyl, aryl, heteroaryl, fluoro, hydroxyl or alkoxy;
ii) CH$_2$C(R$^6$R$^7$)CH$_2$, where R$^6$ and R$^7$ are each independently alkyl, perfluoroalkyl, aryl, or fluoro, or R$^6$ and R$^7$ are connected together to form a carbocyclic or heterocyclic ring;
iii) CH$_2$OCH$_2$, CH$_2$C(O)CH$_2$, or CH$_2$CH$_2$; and
iv) R$^5$ is a carbocyclic, heterocyclic, aryl or heteroaryl ring; and
R$^8$ and R$^9$ are independently selected from the group consisting of hydrogen, alkyl, perfluoroalkyl, alkoxy, aryl and heteroaryl, or R$^8$ and R$^9$ are connected together to form a carbocyclic or heterocyclic ring.

12. A compound of the general formula 25

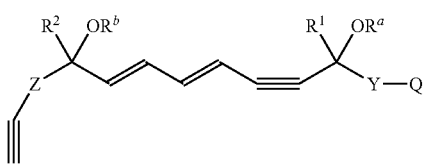

25 wherein:
R$^a$ and R$^b$, are independently selected from the group consisting of hydrogen, alkyl, aryl, heteroaryl, acyl, silyl, alkoxyacyl and aminoacyl;
R$^1$ and R$^2$ are independently selected from the group consisting of hydrogen, alkyl, perfluoroalkyl, aryl and heteroaryl;
Q is selected from the group consisting of:
—C(O)-A, —SO$_2$-A, —PO(OR)-A, where A is hydroxyl, alkoxy, aryloxy, amino, alkylamino, dialkylamino, or —OM, where M is a cation selected from the group consisting of ammonium, tetra-alkyl ammonium, Na, K, Mg, and Zn, and R is hydroxyl or alkoxy; and
Y and Z are linkers independently selected from the group consisting of a ring containing up to 20 atoms and a chain of up to 20 atoms, provided that Y, Z and W can independently include one or more nitrogen, oxygen, sulfur or phosphorous atoms, and further provided that Y, Z and W can independently include one or more substituents selected from the group consisting of hydrogen, alkyl, alkenyl, alkynyl, aryl, heteroaryl, chloro, iodo, bromo, fluoro, hydroxyl, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, and sulfonyl, and further provided that Y, Z and W can also contain one or more fused carbocyclic, heterocyclic, aryl or heteroaryl rings, and provided that all linkers Y are connected to the adjacent C(R)OR group via a carbon atom.

13. The compound according to claim 12, wherein Y is propylene and Z is methylene.

14. A pharmaceutical composition comprising an effective amount of a compound according to claim 8; and a pharmaceutically acceptable carrier.

15. A pharmaceutical composition comprising an effective amount of a compound according to claim 9; and a pharmaceutically acceptable carrier.

16. A pharmaceutical composition comprising an effective amount of a compound according to claim 10; and a pharmaceutically acceptable carrier.

17. A pharmaceutical composition comprising an effective amount of a compound according to claim 11; and a pharmaceutically acceptable carrier.

18. A pharmaceutical composition comprising an effective amount of a compound according to claim 12; and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 7,582,785 B2 | Page 1 of 1 |
| APPLICATION NO. | : 11/093757 | |
| DATED | : September 1, 2009 | |
| INVENTOR(S) | : Petasis | |

It is certified that error appears in the above-identified patent and that said Letters Patent is hereby corrected as shown below:

On the title page,

[*] Notice:   Subject to any disclaimer, the term of this patent is extended or adjusted under 35 USC 154(b) by (433) days Delete the phrase "by 433 days" and insert -- by 944 days --

Signed and Sealed this

Sixth Day of April, 2010

David J. Kappos
*Director of the United States Patent and Trademark Office*